United States Patent
Reisner et al.

(10) Patent No.: US 7,270,810 B2
(45) Date of Patent: Sep. 18, 2007

(54) VETO CELLS EFFECTIVE IN PREVENTING GRAFT REJECTION AND DEVOID OF GRAFT VERSUS HOST POTENTIAL

(75) Inventors: Yair Reisner, Tel Aviv (IL); Massimo Martelli, Perugia (IT)

(73) Assignee: Yeda Research and Development Co. Ltd., Rehovot (IL)

( * ) Notice: Subject to any disclaimer, the term of this patent is extended or adjusted under 35 U.S.C. 154(b) by 700 days.

(21) Appl. No.: 10/169,028

(22) PCT Filed: Dec. 28, 2000

(86) PCT No.: PCT/IL00/00872

§ 371 (c)(1),
(2), (4) Date: Jun. 27, 2002

(87) PCT Pub. No.: WO01/49243

PCT Pub. Date: Jul. 12, 2001

(65) Prior Publication Data

US 2003/0003083 A1    Jan. 2, 2003

(51) Int. Cl.
*A61K 48/00* (2006.01)
*C12N 5/00* (2006.01)
*C12N 5/08* (2006.01)

(52) U.S. Cl. .................. 424/93.1; 424/93.21; 435/366; 435/372; 435/325

(58) Field of Classification Search .............. 424/93.1, 424/93.21; 435/366, 372, 325
See application file for complete search history.

(56) References Cited

U.S. PATENT DOCUMENTS

| | | | |
|---|---|---|---|
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio |
| 4,666,828 A | 5/1987 | Gusella |
| 4,683,202 A | 7/1987 | Mullis |
| 4,801,531 A | 1/1989 | Frossard |
| 4,879,219 A | 11/1989 | Wands et al. |
| 5,011,771 A | 4/1991 | Bellet et al. |
| 5,192,659 A | 3/1993 | Simons |
| 5,272,057 A | 12/1993 | Smulson et al. |
| 5,281,521 A | 1/1994 | Trojanowski et al. |

6,544,506 B2 * 4/2003 Reisner ..................... 424/93.1

OTHER PUBLICATIONS

Kaufman et al. (1995) Annu. Rev. Immunol., vol. 13, 339-367.*
Jacobsen and Claesson (1998) APMIS, vol. 106, 345-353.*
Cavazzano-Calvo et al. (1994) Blood, vol. 83(1), 288-298.*
Reisner et al. (1998) Blood, vol. 92(10), 265a.*
Bachar-Lustig et al "Induction of donor-type chimerism and transplantation tolerance across major histocompatibility barriers in sublethally irradiated mice by Sca-1(+)Lin(−) bone marrow progenitor cells: synergism with non-alloreactive (host x donor)F(1) T cells", *Blood.* Nov. 1, 1999;94(9):3212-21.
Miller, RG, "An immunological suppressor cell inactivating cytotoxic T-lymphocyte precursor cells recognizing it", *Nature.* Oct. 9, 1980;287(5782):544-6.
Kaufman et al, "Phenotypic characterization of a novel bone marrow-derived cell that facilitates engraftment of allogeneic bone marrow stem cells", *Blood.* Oct. 15, 1994;84(8):2436-46.
Pierce et al, "Do donor cells function as veto cells in the induction and maintenance of tolerance across an MHC disparity in mixed lymphoid radiation chimeras?" *Transplantation.* Apr. 1993;55(4):882-7.
Cobbold et al "Monoclonal antibodies to promote marrow engraftment and tissue graft tolerance", *Nature.* Sep. 11-17, 1986;323(6084):164-6.
Goodwin et al, "Isolation of cell lines possessing functional and serological properties resembling those of thymocyte precursors", *Nature.* Sep. 1-17, 1986; 323(6084):166-9.
Sugiura et al, "Wheat germ agglutinin-positive cells in a stem cell-enriched fraction of mouse bone marrow have potent natural suppressor activity", *Proc Natl Acad Sci U S A.* Jul. 1988;85(13):4824-6.
Hiruma et al., "Clonal deletion of postthymic T cells: veto cells kill precursor cytotoxic T lymphocytes," *J Exp Med.* Mar. 1, 1992;175(3):863-8.
Pierce et al, "Thy 1+ donor cells function as veto cells in the maintenance of tolerance across a major histocompatibility complex disparity in mixed-lymphoid radiation chimeras", *Transplant Proc.* Feb. 1993;25(1 Pt 1):331-3.
Strober et al, "Cloned natural suppressor cells prevent lethal graft-vs-host disease", *J Immunol.* Feb. 1, 1987;138(3):699-703.
Tscherning et al "Veto-like down-regulation of T helper cell reactivity in vivo by injection of semi-allogeneic spleen cells", *Immunol Lett.* Aug. 1991;29(3):223-7.
Cassell et al, "Regulation of the cytotoxic T lymphocyte response against Qa-1 alloantigens", *J Immunol.* Jun. 1, 1990;144(11):4075-81.
Claesson et al "Antiself suppressive (veto) activity of responder cells in mixed lymphocyte cultures", *Curr Top Microbiol Immunol.* 1986;126:213-23.

(Continued)

*Primary Examiner*—Anne M. Wehbé

(57) ABSTRACT

A method of transplanting a transplant derived from a donor into a recipient is disclosed. The method comprises the steps of (a) transplanting the transplant into the recipient; and (b) administering to the recipient a dose including non-alloreactive anti-third party cytotoxic T-lymphocytes (CTLs), wherein the non-alloreactive anti-third party CTLs are generated by directing T-lymphocytes of the donor against a third party antigen or antigens, the dose is substantially depleted of T-lymphocytes capable of developing into alloreactive CTLs, thereby preventing or ameliorating both graft rejection by the recipient and graft versus host disease.

55 Claims, 8 Drawing Sheets

OTHER PUBLICATIONS

Fink et al, "Cloned cytolytic T cells can suppress primary cytotoxic responses directed against them" *J Immunol.* Oct. 1984;133(4):1775-81.

Tscherning et al, "Veto suppression: the peripheral way of T cell tolerization", *Exp Clin Immunogenet.* 1993;10(4):179-88.

Claaesson, MH, "Veto cell H-2 antigens: veto cell activity is restricted by determinants encoded by K, D, and I MHC regions", *Cell Immunol.* Oct. 15, 1987;109(2):360-70.

Sambhara et al, "Programmed cell death of T cells signaled by the T cell receptor and the alpha 3 domain of class I MHC", *Science.* Jun. 7, 1991;252(5011):1424-7.

Sambhara et al, "Reduction of CTL antipeptide response mediated by CD8+ cells whose class I MHC can bind the peptide", *J Immunol.* Feb. 1, 1994;152(3):1103-9.

Hiruma et al, "Clonal deletion of postthymic T cells: veto cells kill precursor cytotoxic T lymphocytes", *J Exp Med.* Mar. 1, 1992;175(3):863-8.

Qi et al, Hybrid antibody mediated veto of cytotoxic T lymphocyte responses. *J Exp Med.* May 1, 1996;183(5):1973-80.

Asiedu et al, "Immunoregulatory role of CD8alpha in the veto effect", *Transplantation.* Feb. 15, 1999;67(3):372-80.

George et al, "The molecular mechanisms of veto mediated regulation of alloresponsiveness", *J Mol Med.* Jul. 1999;77(7):519-26.

Reisner et al, "Non Alloreactive Donor Anti-Third Party CTLs Facilitate BM Allografts Across Major Histocompatibility Barriers in Sublethally Irradiated Mice", *Blood*, 92:265a, 1998.

Reich-Zeliger et al, "Enhancement of BM Allografts by Non-Alloreactive Donor CTL's: CD8 Binding and Fas-FasL Apoptosis Mediate the Veto Effect", *Blood*, 94(10) S. 1, 1999.

Aversa et al, "Treatment of high-risk acute leukemia with T-cell-depleted stem cells from related donors with one fully mismatched HLA haplotype", *N Engl J Med.* Oct. 22, 1998;339(17):1186-93.

Hillyer et al, "Peripheral blood stem cell acquisition by large-volume leukapheresis in growth factor-stimulated and unstimulated rhesus monkeys: development of an animal model", *Exp Hematol.* Oct. 1993;21(11):1455-9.

Bachar-Lustig et al, "Murine and Human Non-Alloreactive Anti-3rd Party CTL: A Novel Facilitating Cell With Markedly Reduced GVH Reactivity", *Blood*, 96(111):3739 (Abstract No. 1610), 2000.

Reich-Zeliger et al, "Anti-third party CD8+ CTLs as potent veto cells: coexpression of CD8 and FasL is a prerequisite", *Immunity.* Oct. 2000;13(4):507-15.

Gilboa et al, "Transfer And Expression Of Cloned Genes Using Retroviral Vectors", *BioTechniques*, 4(6):504-512, 1986.

Fink et al, "Veto Cells", *Ann Rev Immunol*, 6:115:-137, 1988.

Lapidot et al, "Enhancement of T-cell-depleted bone marrow allografts in the absence of graft-versus-host disease is mediated by CD8+ CD4− and not by CD8− CD4+ thymocytes", *Blood.* Nov. 1, 1992;80(9):2406-11.

\* cited by examiner

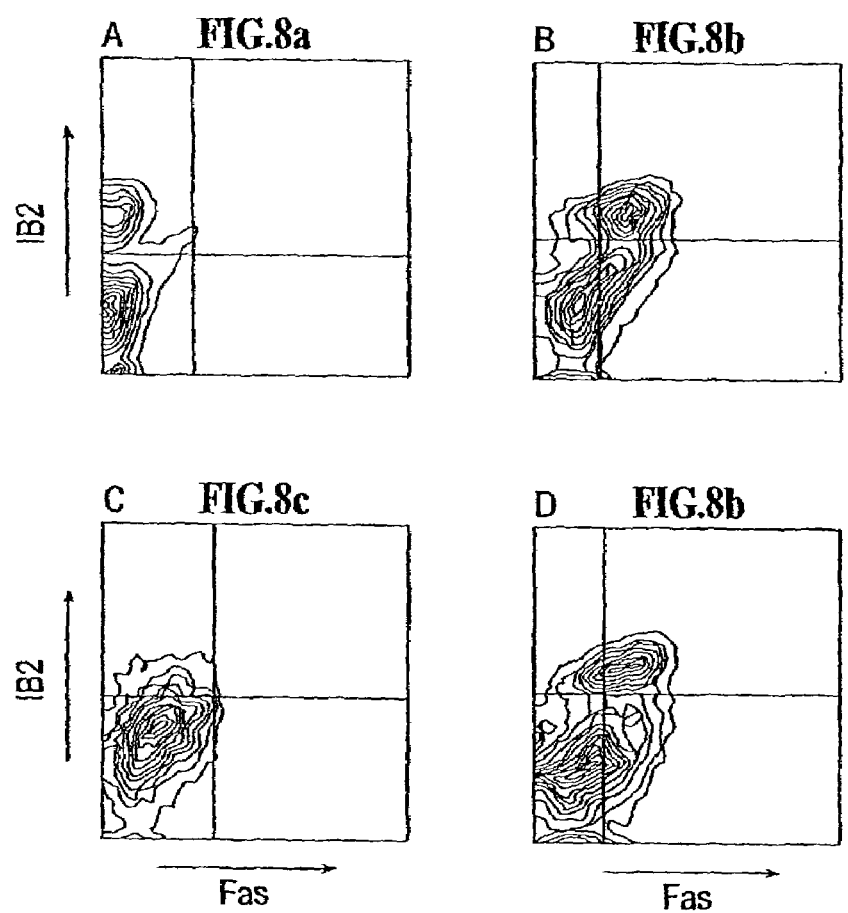
FIG. 8a / FIG. 8b / FIG. 8c / FIG. 8b
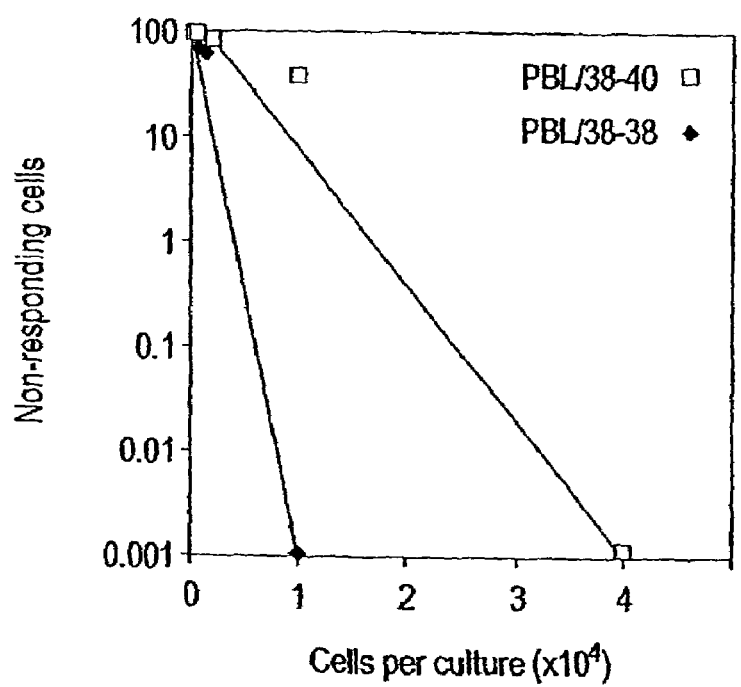
FIG. 9

Fig B: The CTL does not inhibit killing of the same responders against the 3rd party cell

VETO CELLS EFFECTIVE IN PREVENTING GRAFT REJECTION AND DEVOID OF GRAFT VERSUS HOST POTENTIAL

CROSS REFERENCES TO RELATED APPLICATIONS

This Application is a National Phase of PCT Patent Application No. PCT/IL00/00872, filed on Dec. 28, 2000, which claims the benefit of U.S. patent application Ser. No. 09/477,737, filed on Jan. 5, 2000, now U.S. Pat. No. 6,544,506. The contents of the above Applications are hereby incorporated by reference.

FIELD AND BACKGROUND OF THE INVENTION

The present invention relates to veto cell preparations, methods of their manufacture and transplantation method using same which can be used to prevent or ameliorate immune rejection of donor organs, tissues or cells without inducing graft versus host disease (GVHD). More particularly, the present invention relates to a cell preparation for use in transplantation which preparation includes cells which are functional as veto cells but which are substantially devoid of alloreactive cells.

Transplantation of allogeneic and xenogeneic organs, tissues and cells is commonly practiced in humans in order to alleviate numerous disorders and diseases.

For example, bone marrow (BM) transplantation is increasingly used to treat a series of severe diseases in humans, such as for example, leukemia. However, bone marrow transplantation is limited by the availability of suitable donors, since transplanted tissues must traverse major histocompatibility barriers which can otherwise lead to graft rejection.

In view of such limitations, several approaches for enhancing graft acceptance have been suggested.

In one approach, cancer patients receiving autologous BM transplantation were treated with granulocyte colony-stimulating factor (G-CSF), resulting in mobilization of pluripotential stem cells from the marrow to the blood thereby increasing the number of cells which can be collected for autologous transplantation.

In another approach, major histocompatibility barriers in BM transplantation in leukemia patients were overcome by using a very large dose of stem cells, preferably a dose at least 3-fold greater than conventional doses used in T-cell-depleted BM transplantation, in particular a megadose of CD34+ hematopoietic progenitors (U.S. Pat. No. 5,806,529 to Reisner et al.).

Although the megadose approach facilitated permanent acceptance of allogeneic donor type skin grafts in mice 1, such an approach is not readily applicable for human transplantation since the number of stem cells which are required to attain this desirable goal may not be easily collected from human donors.

A difficult barrier for the engraftment of donor hematopoietic cell transplantation arises from the marked level of host hematopoietic and immune cells surviving mild preparatory regimens. Several studies have shown that this challenge can be successfully addressed in rodents by using large doses of bone marrow cells, adequately depleted of T-cells and utilized in conjunction with one form or another of tolerance inducing cells, also termed as veto cells.

Veto cell activity is defined as the capacity to specifically suppress cytotoxic T-cell precursors (CTL-p) directed against antigens of the veto cells themselves, but not against third party antigens 2 Several veto cells or bone marrow transplantation facilitating cells capable of suppressing cytotoxic T-cell precursors have been described[3-11]

Interestingly, it has been shown that some of the most potent veto cells are of T-cell origin, and in particular a very strong veto activity was documented for CD8+ CTL lines or clones[12-16].

The specificity of CTL veto cells was demonstrated by several studies to be unrelated to their T-cell receptor specificity[17-19].

The suppression of effector CTL-p directed against the veto cells is both antigen-specific and MHC-restricted. This suppression results from the unidirectional recognition of the veto cell by the responding cytotoxic T-lymphocytes 18. Furthermore, it has been shown that this suppression is mediated by apoptosis[18, 20].

Blocking experiments conducted with anti-CD8 or anti class I antibodies indicated that the elimination of host anti-donor CTL-p is induced via an interaction of CD8 molecules on the CTL veto cells with the a3 domain of class I molecules on the host CTL-p's [18]. Support to this observation was provided by studies in which CD8 eDNA was introduced into clones lacking CD8 [18]. Further support was provided by experiments which demonstrated that CD8 molecules on the veto cells can directly induce apoptosis in effector cells [21]. More recently, Asiedu et al. demonstrated that antibody mediated cross linking of CD8 on primate bone marrow veto cells, leads to an increased TGFβ production which induces apoptosis in the effector cells [22]. Alternatively, it has been suggested that mouse bone marrow veto cells can induce apoptosis via Fas-Fas-L interaction [23].

The studies described hereinabove demonstrated that veto T-cell preparations can greatly facilitate graft tolerance in bone marrow transplantation. However, the veto T-cell preparations are inadequate for generating graft tolerance since such preparations still include a substantial amount of alloreacting donor T-cells which can lead to GVHD, thus limiting the successful implementation of this approach.

Reisner et al., [24, 28] describe the preparation of non-alloreactive anti-third party CTLs which can be used to enhance graft acceptance in mice. However, following the publication of this abstract and a more careful study, it was realized that the CTL preparation described therein is not depleted of T-cells capable of developing post transplantation into anti-host CTLs inflicting GVHD. Thus, this approach per se is not applicable for application in humans.

There is thus a widely recognized need for, and it would be highly advantageous to have, a novel veto cell preparation devoid of alloreactivity which can be used for substantially reducing rejection of transplanted organs, tissues or cells without generating GVHD, thereby leading to durable tolerance towards the transplanted, organs tissues or cells.

SUMMARY OF THE INVENTION

According to one aspect of the present invention there is provided a method of transplanting a transplant derived from a donor into a recipient, the method comprising the steps of (a) transplanting the transplant into the recipient; and (b) administering to the recipient a dose including non-alloreactive anti-third party cytotoxic T-lymphocytes (CTLs), wherein the non-alloreactive anti-third party CTLs are generated by directing T-lymphocytes of the donor against a third party antigen or antigens, the dose is substantially depleted of T-lymphocytes capable of developing into alloreactive CTLs, thereby preventing or ameliorating both graft rejection by the recipient and graft versus host disease.

According to another aspect of the present invention there is provided a method of treating a recipient suffering from a disease requiring immature hematopoietic cell transplantation, the method comprising the steps of (a) conditioning the recipient under sublethal, lethal or supralethal conditions; (b) administering to the recipient a first dose including immature hematopoietic cells including stem cells from an allogeneic or xenogeneic donor; and (c) administering to the recipient a second dose including non-alloreactive anti-third party cytotoxic T-lymphocytes (CTLs), wherein the CTLs are generated by directing T-lymphocytes derived from the donor against a third party antigen or antigens, the second dose is substantially depleted of T-lymphocytes capable of developing into alloreactive CTLs, thereby preventing or ameliorating both graft rejection and graft versus host disease.

According to yet another aspect of the present invention there is provided a method of producing non-alloreactive anti-third party cytotoxic T-lymphocytes (CTLs), the method comprising the step of directing T-lymphocytes against a third party antigen or antigens, and substantially depleting T-lymphocytes capable of developing into alloreactive CTLs.

According to still another aspect of the present invention there is provided a cell preparation for transplantation to a recipient, the cell preparation comprising donor derived non-alloreactive anti-third party cytotoxic T-lymphocytes (CTLs) directed against a third party antigen or antigens, the cell preparation being substantially depleted of T-lymphocytes capable of developing into alloreactive CTLs.

According to an additional aspect of the present invention there is provided a cell preparation for transplantation to a recipient, the cell preparation comprising (a) donor derived immature hematopoietic cells including stem cells; and (b) donor derived, non-alloreactive anti-third party cytotoxic T-lymphocytes (CTLs) directed against a third party antigen or antigens, the cell preparation being substantially depleted of T-lymphocytes capable of developing into alloreactive CTLs.

According to further features in preferred embodiments of the invention described below, the dose, T-lymphocytes or preparation is substantially depleted of CD4 T cells and/or CD56 natural killer cells.

According to still further features in the described preferred embodiments depletion of T-lymphocytes capable of developing into alloreactive CTLs is effected by deprivation of a factor which is (i) required for CTLs maturation; and (ii) secreted by maturing CTLs.

According to still further features in the described preferred embodiments the factor is a cytokine.

According to still further features in the described preferred embodiments the cytokine is IL2.

According to still further features in the described preferred embodiments depletion of T-lymphocytes capable of developing into alloreactive CTLs is effected by affinity labeling followed by label based separation.

According to still further features in the described preferred embodiments depletion of T-lymphocytes capable of developing into alloreactive CTLs is effected by affinity purification.

According to still further features in the described preferred embodiments the donor is selected from the group consisting of an allogeneic donor either HLA identical or HLA non-identical and a xenogeneic donor.

According to still further features in the described preferred embodiments the recipient is a human.

According to still further features in the described preferred embodiments the recipient and the donor are both humans.

According to still further features in the described preferred embodiments the third party antigen or antigens is selected from the group consisting of third party cells, a cell antigen, a viral antigen, a bacterial antigen, a protein extract and a purified protein. In a presently preferred embodiment the third party antigen are synthetic peptides which constitute viral antigens and which are presented by autologous antigen presenting cells pulsed therewith.

According to still further features in the described preferred embodiments the viral antigen is an EBV or a CMV antigen.

According to still further features in the described preferred embodiments the purified protein is ovalbumin.

According to still further features in the described preferred embodiments the third party cells are allogeneic or xenogeneic cells with respect to the recipient.

According to still further features in the described preferred embodiments the allogeneic cells have HLA antigens different from that of the donor but which are not cross reactive with the recipient HLA antigens.

According to still further features in the described preferred embodiments the allogeneic cells are stimulatory cells selected from the group consisting of cells purified from peripheral blood lymphocytes (PBLs), spleen or lymph nodes, cytokine-mobilized PBLs and in vitro expanded antigen-presenting dendritic cells (APC).

According to still further features in the described preferred embodiments the immature hematopoietic cells including stem cells are derived from the bone marrow, mobilized peripheral blood, fetal liver, yolk sac and/or cord blood of the donor.

According to still further features in the described preferred embodiments the mobilized peripheral blood cells are obtained by leukapheresis of peripheral blood of the donor after stimulation with a suitable cytokine.

According to still further features in the described preferred embodiments the immature hematopoietic cells are T-cell depleted hematopoietic progenitor cells.

According to still further features in the described preferred embodiments the T-cell depleted hematopoietic progenitor cells are CD34+ progenitor hematopoietic cells.

According to still further features in the described preferred embodiments a cell ratio between the cytotoxic T-lymphocytes and the immature hematopoietic cells including stem cells is at least 1 to 100, preferably 1.5 to 100.

According to still further features in the described preferred embodiments the cell number of the cytotoxic T-lymphocytes infused to a recipient is more than $5 \times 10^6$/Kg body weight and the immature hematopoietic cells including stem cells (CD34 cells) is more than $1.0 \times 10^6$/Kg body weight.

According to still further features in the described preferred embodiments steps of transplanting and administering are effected at the same time, or alternatively, the step of transplanting is performed either prior to, or after the step of administering.

The present invention successfully addresses the shortcomings of the presently known configurations by providing veto cells which are highly effective in preventing graft rejection, yet are devoid of graft versus host disease potential.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this re, no attempt is made to show details of the invention in more detail than is necessary for a fundamental understanding of the invention, the description taken with the drawings making apparent to those skilled in the art how the several forms of the invention may be embodied in practice.

In the drawings:

FIGS. 8a-d depict the deletion of anti-H2$^d$ T-cells by non-alloreactive anti-third party CTLs. Splenocytes from 2c transgenic mice (H-2$^b$) bearing transgene TCR specific against H-2$^d$ were stimulated in MLR against Balb/c splenocytes (H-2$^d$). Expression of Fas on CD8 transgenic (1B2$^+$) T cells was analyzed by FACS before MLR (FIG. 8a) and at 48 hr (FIG. 8b). Deletion of Fas$^+$ 1B2$^+$ CD8 T-cells following addition to the MLR culture of Balb anti-C3H (FIG. 8c) or SJL anti-C3H (FIG. 8d) CTLs, was determined at 48 hrs after initiation of the MLR.

FIG. 9 is a graph depicting the relationship between cells per culture and the % of non-responding cells of unmanipulated peripheral blood lymphocytes (PBLs) taken from a donor (R) and stimulated against potential host type PBL (patient No. 38). The specific killing of HLA-unrelated cell types (patient No. 40) was demonstrated to be negligible (square), while killing was maintained at high potency against the original stimulators (diamond and circle).

FIG. 11a shows the inhibition of specific lysis at 1:25 and 1:50 veto to effector cell ratio, compared to a control experiment FIG. 11b) using the same veto cells in a non-relevant MLR, directed against an irrelevant stimulator bearings different HLA antigens.

DESCRIPTION OF THE PREFERRED EMBODIMENTS

Figure 1:
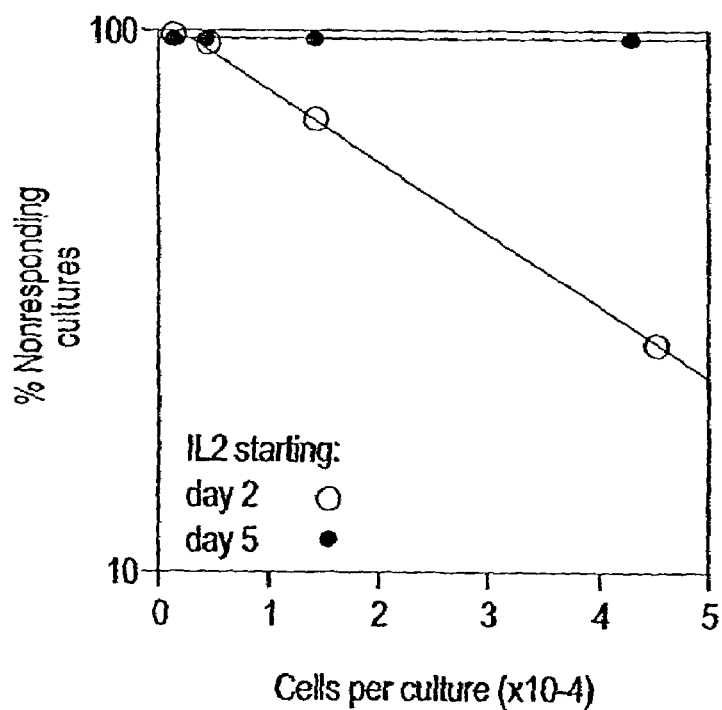
FIG. 1 is a graph depicting the level of anti-host CTLp in donor anti-third party CTL lines prepared with and without IL2 starvation.

The present invention is of veto cell preparations, methods for their production and their use in transplantations, which veto cells can be used to induce durable tolerance of donor organs, tissues or cells without inducing GVHD. Specifically, the present invention relates to veto cell preparations for use in transplantation, which veto cell preparations include cells which are functional as veto cells but which are substantially devoid of alloreactive cells and as such, when introduced into a recipient, these veto cells prevent graft rejection without inducing GVHD.

The principles and operation of the present invention may be better understood with reference to the drawings and accompanying descriptions.

Before explaining at least one embodiment of the invention in detail, it is to be understood that the invention is not limited in its application to the details set forth in the following description. The invention is capable of other embodiments or of being practiced or carried out in various ways. Also, it is to be understood that the phraseology and terminology employed herein is for the purpose of description and should not be regarded as limiting.

Early studies in murine models and more recent clinical data in heavily pre-treated Leukemia patients have shown that escalation of hematopoietic progenitor cells can overcome major genetic barriers and enable rapid and durable engraftment of haploidentical 3-loci mismatched transplants without inducing GVHD. In vitro studies suggest that veto cells within the CD34 progenitors population likely mediate this facilitating effect.

The "megadose" concept was also shown recently to be useful for tolerance induction in sublethally irradiated mice by overcoming the marked resistance presented by the large number of lymphocytes surviving the sublethal conditioning. Allogeneic chimera generated by transplantation of a megadose of $Sca1^{+\ Lin-}$ cells, permanently accept allogeneic donor type skin grafts.

However, the numbers required to attain this desirable goal may not be easily collected from human donors.

Non-alloreactive, Peanut Agglutinin negative thymocytes from (host×donor) F1 which are non-alloreactive by virtue of their genetic composition, were also shown to enhance engraftment of T-cell depleted BM.

More recently these cells were shown to synergise with murine $Sca1^+$ $Lin^-$ cells so as to reduce the minimal number of cells required to achieve induction of substantial mixed chimerism in the sub lethal mouse model.

In humans, non-alloreactive T-cells can be generated by purging interleukin-2 receptor (CD25) MLR reactive T-cells or by anergy induction upon incubation with CTLA-4. However, these approaches, which make use of T-cell stimulation with the very antigens against which tolerance is desired, might involve some risk for generating committed CTLs, if any of the CTL progenitors escape deletion or anergy induction. Once such anti-host CTLs are generated, it is very difficult to suppress their alloreactivity in vivo.

An alternative approach is based on earlier studies which showed that $CD8^+$ CTL clones possess extremely high veto activity.

Donor derived T-lymphocytes exposed to a third party antigen proved useful in generating CTLs effective in preventing or ameliorating graft rejection, however, such CTL preparations included a substantial fraction of donor derived T-lymphocytes which could develop into alloreactive donor CTLs, inducing GVHD.

Thus, all prior art approaches which utilize veto cells of T-cell origin fail to provide adequate solution for inducing graft acceptance since such veto cell preparations include a substantial amount of alloreactive T-cells which induce GVHD in the host following administration.

While reducing the present invention to practice, donor anti-third party CTLs which are depleted of anti-host alloreactivity were generated. In the preferred embodiments of the invention cell preparations are also substantially depleted of CD4 T cells and/or CD56 natural killer cells, preferably both.

As is further described in Examples 1 and 2 of the Examples section below, depletion of cells having a potential of becoming alloreactive (anti-host) CTLs from a donor anti-third party CTLs culture involved, in the specific example provided, initial IL-2 starvation which resulted in apoptosis of non-induced T-cells present in the culture. Studies utilizing such mouse and human CTL preparations which were performed in-vitro, demonstrated that such non-alloreactive CTL preparations are depleted of cells having the potential of maturing into anti-host CTLs.

Thus, according to one aspect of the present invention there is provided a method of transplanting a transplant derived from a donor into a recipient.

As used herein the terms "transplant" or "graft" refers to either allogeneic or xenogeneic transplants or grafts including, but not limited to whole organs, such as for example, kidney, heart, liver or skin; tissues, such as, for example, tissues derived from an organ such as a liver; or cells, such as, for example, immature hematopoietic cells.

As used herein the term "allogeneic" refers to as being from the same species. As such an "allograft" is a transplant between two individuals of the same species which individuals display strong (unrelated individuals) or weak (haploidentical siblings) histocompatibility differences.

As used herein the terms "xenogeneic" or "heterogeneic" refer to as being from two different species. As such a "xenograft" or a "heterograft" is a transplant between two individuals of a different species.

Thus, the method according to the present invention, which is further described and exemplified hereinbelow, can be utilized for transplantation of an organ such as a kidney or a heart to a recipient suffering from, for example, renal or heart failure, or for the transplantation of liver, lung or skin tissue to a recipient suffering from hepatic or lung failure or skin damage (e.g., burns).

The method described below can also be used, for example, for treating a recipient suffering from a disease requiring immature hematopoietic cell transplantation.

In the latter case, immature allogeneic or xenogeneic hematopoietic cells (including stem cells) which can be derived, for example, from bone marrow, mobilized peripheral blood (by for example leukapheresis), fetal liver, yolk sac and/or cord blood of the donor and which are preferably T-cell depleted $CD34^+$ immature hematopoietic cells, can be transplanted to a recipient suffering from a malignant disease. Such a disease can be, but is not limited to, leukemia such as acute lymphoblastic leukemia (ALL), acute non-lymphoblastic leukemia (ANLL), acute myelocytic leukemia (AML) or chronic myelocytic leukemia (CML), and severe combined immunodeficiency syndromes (SCID), including adenosine deaminase (ADA), osteopetrosis, aplastic anemia, Gaucher's disease, thalassemia and other congenital or genetically-determined hematopoietic abnormalities.

Regardless of the transplant type, to avoid graft rejection, the method according to the present invention also utilizes a novel veto cell preparation which includes non-alloreactive anti-third party cytotoxic T-lymphocytes (CTLs). Such CTLs are generated by conditioning donor derived T-cells against third party antigens. This CTL cell preparation functions in reducing graft rejection by the recipient. Further detail of such a CTL preparation is given in Examples 1-3 of the Examples section. Such preparations are depleted of T-lymphocytes capable of developing into alloreactive CTLs, thereby preventing or ameliorating both graft rejection by the recipient and graft versus host disease.

As used herein the phrase "non-alloreactive" refers to having substantially no reactivity against the donor or recipient.

According to the method of the present invention, these CTLs are administered either concomitantly, prior to, or following the transplantation of the donor transplant.

In the case of hematopoietic cell transplantation, the cell ratio between the cytotoxic T-lymphocytes and the immature hematopoietic cells including stem cells is at least 1 to 100, preferably, in the range of 1 to 1-5 to 1, more preferably about. Preferably, the cell number of the cytotoxic T-lymphocytes infused to a recipient is more than $5 \times 10^6$/Kg body weight and the immature hematopoietic cells including stem cells (CD34 cells) is more than $1.0 \times 10^6$/Kg body weight.

As used herein the phrase "third party antigen or antigens" refers to antigens which are not present in either the donor or recipient.

For example, third party antigens can be antigens of viruses, such as for example, Epstein-Barr virus (EBV) or cyto-megalo virus (CMV) or of third party cells (cells not from the donor or recipient). Viral antigens can be presented by cells (e.g., cell line) infected therewith or otherwise made to express viral proteins. Autologous antigen presenting cells can be used to present short synthetic peptides fused or loaded thereto. Such short peptides may be viral derived peptides or peptides representing any other antigen. Dedicated software can be used to analyze viral or other sequences to identify immunogenic short peptides, i.e., peptides presentable in context of class 1 MHC or class 1 MHC.

Third party cells can be either allogeneic or xenogeneic with respects to the recipient. Preferably, in the case of allogeneic third party cells, such cells have HLA antigens different from that of the donor but which are not cross reactive with the recipient HLA antigens, such that CTLs generated against such cells are not reactive against transplant or recipient antigens.

According to another preferred embodiment of the present invention the allogeneic third party cells are stimulatory cells selected from the group consisting of cells purified from PBL, spleen or lymph nodes, cytokine-mobilized PBLs and in vitro expanded antigen-presenting dendritic cells (APC).

Third party antigens can be presented on the cellular, viral or bacterial surfaces or derived and/or purified therefrom. Additionally, a viral antigen can be displayed on an infected cell and a cellular antigen can be displayed on an artificial vehicles such as a liposome.

In addition, third party antigens can, for example, be proteins extracted or purified from a variety of sources. An example of a purified protein which can serve as a third party antigen according to the present invention is ovalbumin. Other examples are envisaged.

According to the present invention, the CTLs are preferably generated against third party cells or viruses or virally infected or viral peptides presenting cells and as such, the third party antigens utilized by the present invention are various native cellular or viral antigens or a combination of both which are displayed on the surface of the cell or virus.

Utilizing cells, viruses, virally infected or viral peptides presenting cells as third party antigens is particularly advantageous since such third party antigens include a diverse array of antigenic determinants and as such direct the formation of CTLs of a diverse population, which may further serve in faster reconstitution of T-cells in cases where such reconstitution is required, e.g., following lethal or sublethal irradiation procedure. Furthermore, when CTLs are directed against viral infected cells, it is plausible to obtain at least some graft versus cancer cells activity due to cross reactivity between viral antigens and cancer cell associated or specific antigens.

Thus, as already mentioned above, the method according to this aspect of the present invention is effected by transplanting the transplant into the recipient along with a non-alloreactive anti-third party cytotoxic T-lymphocytes (CTLs) depleted of T-lymphocytes capable of developing into alloreactive CTLs, thereby preventing or ameliorating both graft rejection by the recipient and graft versus host disease.

Since the non-alloreactive anti-third party CTLs are generated by directing T-lymphocytes derived from the donor against third party antigen or antigens, the resultant CTLs prevent or ameliorate graft rejection by the recipient by trapping and killing recipient CTL progenitors (responders) which are formed against the transplant. Furthermore, since the CTLs are generated against third party antigens, such CTLs are not active against recipient tissues or against the donor transplant. Since the anti-third party CTLs are depleted of T-lymphocytes capable of developing into alloreactive CTLs, they prevent or ameliorate graft versus host disease.

According to a preferred embodiment of the present invention the method of transplanting a donor transplant further includes an additional step in which the recipient is conditioned under sublethal, lethal or supralethal conditions prior to transplantation.

Such conditioning is dependent on the nature of the transplant and the condition of the recipient. The recipient may be conditioned under sublethal, lethal or supralethal conditions, for example, by total body irradiation (TBI) and/or by treatment with myeloablative and immunosuppressive agents according to standard protocols. For example, a sublethal dose of irradiation is within the range of 1-7.5 Gy TBI, a lethal dose is within the range of 7.5-9.5 Gy TBI and a supralethal dose is within the range of 9.5-16.5 Gy TBI. Examples of myeloablative agents are busulphan, dimethyl mileran and thiotepa, and of immunosuppressive agents are prednisone, methyl prednisolone, azathioprine, cyclosporine, cyclophosphamide, fludarabin, etc.

According to the method of the present invention, the recipient is preferably conditioned under sublethal conditions.

As already stated numerous times, the non-alloreactive anti-third party CTLs according to the present invention are substantially depleted of T-lymphocytes capable of developing into alloreactive CTLs, and are therefore said to be "non-alloreactive". As such they differ and are advantageous over prior art veto cells. Depletion of T-lymphocytes capable of developing into alloreactive CTLs is of particular advantage since the presence of alloreactive cells in the recipient can lead to the development of GVHD.

A non-alloreactive anti-third party CTLs cell preparation is generated as described above by directing donor derived T-lymphocytes against third party antigens and the preparation is depleted of T-lymphocytes capable of developing into alloreactive CTLs.

According to one preferred embodiment of the present invention the depletion of T-lymphocytes capable of developing into alloreactive CTLs is effected by depriving T-lymphocytes cultured in the presence of third party antigens of a factor which is (i) required for CTLs maturation or protection from apoptosis; and (ii) secreted by maturing CTLs. Under such culturing conditions T-lymphocytes capable of developing into alloreactive CTLs undergo apoptosis, wherein maturing CTLs present in the culture survive factor deprivation since such cells self secrete (autocrine) this factor.

The factor according to the teachings of the present invention can be for example, a cytokine, such as, but not limited to, IL2. IL2 depravation of CTL preparations is described in detail in Examples 1-3 of the Examples section below.

According to an embodiment of the present invention, depletion of T-lymphocytes capable of developing into alloreactive CTLs is effected by affinity labeling followed by label based separation. Thus, when stimulated against host antigens, a fluorescently labeled anti-CD69 or anti-CD25 antibody which specifically binds the unique activation antigen of T-lymphocytes and/or a fluorescently labeled anti-IL2 or anti-γINF which specifically binds cells secreting these cytokines, can be used to separate anti-host T-lymphocytes from anti-third party CTLs, thereby deplete T-lymphocytes capable of developing into alloreactive CTLs. Such specific labeling can be used to select anti-third party CTL precursors prior to IL-2 starvation or as a substitute for IL-2 starvation.

Such specific labeling can be used to select anti-third party CTL precursors prior to IL-2 starvation or as a substitute for IL-2 starvation.

According to still further features in the described preferred embodiments depletion of T-lymphocytes capable of developing into alloreactive CTLs is effected by affinity purification.

For example, a substrate including an antibody or a ligand capable of specifically binding a cell surface molecule displayed only by T-lymphocytes but not by CTLs or vice versa, can be used to effectively deplete T-lymphocytes capable of developing into alloreactive CTLs from the CTL preparation.

The affinity substrate according to the present invention can be a column matrix such as, for example agarose, cellulose and the like, or beads such as, for example, magnetic beads onto which an anti-T-lymphocyte or an anti-CTLs antibody, as is described above, is immobilized.

Thus, according to this aspect of the present invention, depletion of T-lymphocytes capable of developing into alloreactive CTLs, can be effected via column chromatography or magnetic bead separation.

The purpose in growing donor T cells sensitized against third party antigen or antigens is to achieve a T cell preparation depleted of alloreactive clones directed against host antigens. As is described herein, the procedure includes two major steps. In the first, IL-2 starvation is used to effect partial depletion of cells which cannot produce their own IL-2, in the second major step anti-third party clones are expanded vigorously with optimal doses of IL-2 so as to further deplete remaining anti host clones. In is general, CD8 CTLs are directed against antigens presented in the context of HLA class I, while CD4 helper T cells recognize antigens in the context of HLA Class II. The latter cells lack veto activity and therefore the procedure described herein leads to minimal generation of such cells. However, it was experimentally found that even when using stimulation protocols favoring generation of CTLs against third party antigens, it is difficult to achieve high levels of CD8 CTLs at the end of the culture, unless CD4 T cells and CD56 natural killer (NK) cells are removed 10-16 days after the IL2 starvation period (e.g., prior to stimulation with high levels of IL-2). Thus in a preferred embodiment of the present invention CD8 cells purification is effected by either negative selection for removing CD4 and CD56 cells or by positive selection with for retaining CD8 cells. Such selection can be effected, for example, using affinity solid supports including anti-CD8 antibodies (for positive selection) or anti-CD4 antibodies and anti CD56 antibodies (for positive selection). The solid support can be a column, beads or magnetic beads. Alternatively, such selection can be effected, for example, using affinity labeling followed by FACS separation employing fluorescently labeled anti-CD8 antibodies, anti-CD4 antibodies and/or anti CD56 antibodies.

According to yet an additional aspect of the present invention there is provided a method of transplanting a transplant derived from a donor into a recipient. The method according to this aspect of the present invention is identical to the method described hereinabove with the exception that the veto cells utilized are of non T-lymphocyte origin.

A veto cell preparation according to this aspect of the present invention, includes donor derived, genetically modified non-T-cells expressing recombinant Fas ligand and recombinant CD8 antigen.

As is described in Example 2 of the Examples section, while reducing the present invention to practice it was uncovered that CTLs can veto effectively CTL progenitors only if both Fas-L and CD8 are co-expressed on the former CTLs.

As such, donor derived non-T-lymphocyte circulatory cells, such as, for example, monocytes, neutrophilles or basophilles, can also serve as effective veto cells provided these cells express and display CD8 and Fas-L.

To express these proteins in such cells, the coding sequences of Fas-L and CD8 subunit o (Gene Bank accession Nos.: U11821 and M12825, respectively, both are incorporated herein by reference) including appropriate leader sequences are isolated and each is ligated into a suitable expression cassette of an expression vector construct.

The vector constructs can then be co-introduced into the cell by any one of a variety of methods known in the art. Such methods can be found generally described in Sambrook et al., "Molecular Cloning: A Laboratory Manual", Cold Springs Harbor Laboratory, New York, 1989, Ausubel et al., "Current Protocols in Molecular Biology", John Wiley and Sons, Baltimore, Md., 1989, Chang et al., "Somatic Gene Therapy", CRC Press, Ann Arbor, Mich., 1995, Vega et al., "Gene Targeting", CRC Press, Ann Arbor Mich. (995), "Vectors: A Survey of Molecular Cloning Vectors and Their Uses", Butterworths, Boston Mass., 1988, and Gilboa et al., Biotechniques 4 (6): 504-512, 1986, and include, for example, stable or transient transfection, lipofection, electroporation, biolistic bombardment and infection with recombinant viral vectors.

Each nucleic acid construct according to this aspect of the present invention includes a promoter for regulate the expression of Fas-L or CD8. Such promoters are known to be cis-sequence elements required for transcription as they serve to bind DNA dependent RNA polymerase which transcribes sequences present downstream thereof.

The promoter of choice that is used in conjunction with this aspect of the invention can be any promoter suitable for expression in mammalian cells. Preferably the promoter utilized is a strong, constitutive promoter capable of expressing high levels of the transcripts. In addition, to further increase transcriptional activity the vector construct of the present invention may also include a transcriptional enhancer element.

The vector construct according to this aspect of the present invention preferably further includes an appropriate selectable marker. It will be appreciated that since two independent constructs are utilized herein, each construct includes a unique selectable marker, such that cell transformed with both constructs can be selected for. Alternatively, a single vector harboring both genes, each with its own expression regulatory sequences, is employed.

The vector construct according to the present invention preferably further includes an origin of replication in mammalian cells and an appropriate selectable marker and origin of replication for propagation in E. coli (i.e., shuttle vector). The vector construct of the present invention can be utilized for transient expression (i.e., no genomic integration), or for integration into the genome of transformed cells and expression therefrom. The construct according to this aspect of the present invention can be, for example, a plasmid, a bacmid, a phagemid, a cosmid, a phage, a virus or an artificial chromosome.

It will be appreciated that CD8 and Fas-L can also be expressed from a single vector construct as a single chimeric transcript, provided this transcript includes an IRES sequence for directing the translation of a second polypeptide encoded by the transcript.

Thus according to this aspect of the present invention the method of transplanting a donor transplant utilizes a veto cell preparation of genetically modified non-T-cells expressing recombinant Fas ligand and recombinant CD8 antigen.

It will be appreciated that such a veto cell preparation is inherently advantageous for inducing tolerance of transplants since such a preparation does not include cells of T-lymphatic origin and therefore, such veto cells inherently cannot induce GVHD.

In addition, since such cells are derived from the donor they serve as excellent traps for CTL progenitors generated by the recipient as a response to the transplant and as such prevent or ameliorate transplant/graft rejection.

Thus, this aspect of the present invention describes an alternative approaches to generating non-alloreactive anti-third party veto cells. By expressing Fas-L and CD8, in a variety of cells, these cells can serve as veto cells for antigens against which tolerance induction is desired.

Similarly to the anti-third party CTLs described by other aspects of the present invention, these 'artificial' veto cells could help reduce the effective CD34 megadose requirements in mismatched leukemia patients and may lead to safe mismatched hematopoietic transplants in patients for whom the risk of supralethal radio-chemotherapy is not justified, such as patients with thalassemia, sickle cell anemia and several enzyme deficiencies.

Furthermore, induction of substantial durable chimerism can be used, according to the present invention, to induce tolerance towards organ or tissue transplants, or as a prelude for adaptive cell therapy in cancer patients.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Generation of Donor Anti-Third Party Mouse CTLs: IL-2 Starvation Improves Deletion of Anti-Host CTL Precursors Non-myeloablative conditioning protocols are currently explored in elderly leukemia patients who have HLA identical donors. Engraftment is mediated in these patients by the large number of T-cells present in the unseparated peripheral blood progenitor preparations used for transplantation. Thus, these transplants are associated with limited GVHD and with anti-host reactivity leading to myeloablation of host hematopoiesis. However, for patients who do not have a fully matched donor, T-cell toxicity is more pronounced and rather unacceptable. Removal of alloreactive T-cells from the transplant inoculum is likely to weaken the engraftment potency and to result in a high rate of graft rejection. As such, and as described in this Example, anti-third party CTL preparations devoid of cells capable of maturing into anti-host CTLs were established in order to reduce the rate of rejection and to prevent induction of GVHD.

While reducing the present invention to practice and as is specifically shown herein, the inventors have uncovered that CTL veto cell preparations of a donor type, can be effectively depleted of alloreactivity against host cells by stimulation against third party stimulators by initial exogenous IL-2 starvation. This depletion is due to the fact that only activated CTL precursors (CT's) are capable of surviving the IL-2 starvation in the primary culture. Evidently, this CTL preparation depleted of alloreactivity against the host could potentially facilitate the induction of donor type chimerism without GVHD in sub-lethally irradiated recipients.

In addition, this study, examines the mechanisms responsible for the veto activity mediated by non-alloreactive anti-third party CTLs.

Materials and Methods:

Animals: 6-12 week old female mice were used. C3/HeJ, BALB/c, C57BL/6, gld/C3H/HeJ, lpr/C3H/HeJ were obtained from the Roscoe B. Jackson Memorial Laboratory (Bar Harbor, Me.). A breeding pair of Transgenic H-$2^b$ mice expressing the TCR-ab from the CTL clone 2C with specificity for $L^d$, was kindly provided by Janko Nikolic-Zugic, (Sloan-Kettering, NY). Progeny from these Tg mice and PO mice were bred at the Weizmann Institute Animal Breeding Center (Rehovot, Israel). All mice were kept in small cages (five animals in each cage) and fed sterile food and acid water containing cyprofloxacin (20 µg/ml).

Preparation of non-alloreactive donor anti-third party CTLs: Splenocytes of Balb/c mice (donor responders) were harvested and single cell suspensions were prepared. The cell suspensions were treated with Tris-buffered ammonium chloride to remove red cells and the isolated mononuclear cells ($2 \times 10^6$/ml) were stimulated with irradiated (20 Gy) C57BL/6 or C3H/HeJ (third party stimulators) splenocytes ($2 \times 10^6$/ml), and treated with Tris-buffered ammonium chloride. Responders and stimulators were incubated in a complete tissue culture medium (CTCM) at 37° C. in a 5% $CO_2$/air Heraeus incubator. 5 days following seeding, 20 U/ml of human rhIL-2 (Eurocetus, Milan, Italy) were added to the mixed lymphocyte reaction culture every 24 hours, 2 days later the medium was replaced by a fresh culture medium. 10 days following seeding, the MLR cultures were harvested, fractionated on Ficol-Paque plus (Amersham Pharmacia Biotech AB, Sweden), analyzed by FACS for their CD8 level and added to the MLR cultures at different cell ratios, as described hereinbelow in the results section.

MLR cultures and cytotoxicity assay: Spleen cells of C3H/Hej mice (responders) were harvested and single cell suspensions were prepared as described above. The cells ($2 \times 10^6$/ml) were then stimulated with irradiated (20 Gy) Balb/c splenocytes ($2 \times 10^6$/ml), or with $2 \times 10^6$/ml irradiated (20 Gy) SJL splenocytes. Four-six replicates per group were cultured in 96-well U bottomed plates in 0.2 ml CTCM, for 6 days at 37° C. (5% $CO_2$ atmosphere). ConA blasts generated from SJL or Balb/c spleen cells (2 days in the presence of 2 mg ConA/$2 \times 10^6$ cells/ml) were labeled with $^{51}$Cr (NEN, Boston Mass.). Cell-mediated lysis assay was performed using variable numbers of MLR effector cells and 5000 target cells in 96-well V-bottom plates. $^{51}$Cr release was measured after a 4-h incubation at 37° C. Results are expressed as a specific lysis calculated as follows: % specific lysis=100×((experimental release−spontaneous release)/(maximum release−spontaneous release)). The standard deviation (SD) of replicate values were consistently less than 10% of the mean.

Veto activity of non-alloreactive donor anti-third party CTLs: To determine whether mouse non-alloreactive donor anti-third party CTLs possess veto activity, spleen cells from C3H/HeJ mice ($2 \times 10^6$/ml) were incubated for 6 days with irradiated (20 Gy) allogeneic spleen cells ($2 \times 10^6$/ml) from Balb/c (H-2 matched) or SJL (H-2 mismatch) mice.

Non-alloreactive donor anti-third party Balb/c CTLs were added to the MLC at a 1:100, 1:50 and 1:10 veto: responder cell ratio. The killing activity of the responder CTL-p was determined by $^{51}$Cr-release assay.

Inhibition of the veto effect of CTLs by anti-CD8 mAb: Veto anti-third party CTLs from Balb/c origin were added to the MLR described above, at a final concentration of 2%. Anti-CD8 monoclonal antibody (kindly provided by Uli Hamerling, Sloan-Kettering, NY) directed against Ly-2.2 antigen expressed selectively on the veto cells and not on the effector cells, was added to the MLR at different concentrations as described in results, and the inhibition of the veto effect was monitored.

Deletion of anti-H$2^d$ T-cells by non-alloreactive anti-third party CTLs: Spleen cells of 2C Transgenic H-$2^b$ mice expressing the TCR-ab with specificity for $L^d$ mice (kindly provided by Janko Nikolie-Zugic, Sloan-Kettering, NY), were treated as described above. The cells ($2 \times 10^6$/ml) were then stimulated with irradiated (20 Gy) Balb/c splenocytes ($2 \times 10^6$/ml) in the presence of 2% or 20% veto anti-third party CTLs originated from Balb/c or from SJL (background control) splenocytes. Cultures containing 20% or 2% veto CTLs were continued for 48 hours or 5 days, respectively, in 6-well plates. The deletion of transgenic T-cells was monitored by cytoflourometry, measuring the level of 2C transgenic cells specifically stained by the 1B2 antibody directed against the clonotypic anti-H-2$L^d$ TCR.

Cytoflowmetry: FACS analysis was performed using a modified Becton Dickinson FACScan. Fluorescence data were collected using 3-decade logarithmic amplification on 25-50×$10^3$ viable cells as determined by forward-light-scatter intensity. Cells were stained with a CD8a (Ly-2)FITC, CD3e-PE, CD95 (Fas)-FITC (Phamingen) CD4-Qantum Red (sigma), 1B2 biotinated (kindly provided by Janko Nikolic-Zugic, Sloan-Kettering, NY), R-PE streptavidin (Jackson Immuno Research Lab. Inc.) Vectors for gene transfer: PLNGFP-mock vector was constructed by subcloning gene encoding enhanced green fluorescence protein (EGFP, Clontech) from pEGFP-N1 (Clontech) into EcoRI and HpaI sites of pLXSN provided by A D Miller, St. Jude Children's Research Hospital, Memphis, Tenn.) PLNGFP-Fas-L was also a derivative of pLXSN and was constructed by subcloning of a fragment containing EGFP gene, internal nbosome entry site (IRES) and murine Fas-L cDNA into BamHI and XhoI sites of pLXSN (LTR-EGFP-IRS-mFas-L-SV40p-NeoR).

Packaging of refroviral vectors and virus supernatant production: Plasmid DNA was transfected into ecotropic murine retroviral vector packaging cell line GP-E86 and stably transfected cells were selected with G418. High titter packaging cell lines were isolated by screening individual colonies. Retrovirus supernatant was prepared according to standard procedure.

Gene transfer into splenocytes of Fas-L mutated C3H-gld mice: 50 u/ml of human rhIL-2 were added to a CTL culture generated from "gld" spleen cells. Two days following addition, the stimulated CTLs were resuspended in RPMI-1640 containing 5 mg/ml protamine sulfate and 50 u/ml rhIL-2 and were incubated with viral supernatant which was added daily for 3 days. Forty eight hours following the last addition of the viral supernatant, the infected cells were selected in G418 (450 mg/ml) in the presence of rbIL-2 (50 u/ml) for one week and then tested for their veto activity in MLR as described above.

Experimental Results:

Veto activity of anti-third party CTLs: To evaluate the effect of IL2 starvation on anti-host reactivity of non-alloreactive anti-third party CTLs, Balb/c (H-$2^d$) splenocytes were stimulated, in the presence or absence of recombinant human IL-2 (rhIL-2), against irradiated (20 Gy) C57BL/6 (H-$2^b$, third party) splenocytes in MLR culture for 4 days. On the second day or fifth day of the cell culture rhIL-2 was added and the cells were kept for additional six days. After culture, these cells were harvested and tested for their CTL-p frequency against the intended host (C3H) or the third party used for stimulation (C57BL/6). As can be seen in FIG. 1, following IL2 starvation for 4 days no anti-host CTLp could be detected while a significant frequency of anti-host CTLp was documented when IL2 was added to the MLR culture on the second day.

To evaluate the veto activity of such non-alloreactive C, Balb/c H-$2^d$ splenocytes were stimulated against irradiated (20 Gy) C57BL/6 H-$2^b$ (third party) splenocytes in MLR culture for 10 days, adding rbIL-2 only on the fifth day of the cell culture. Following culturing, these cells were harvested and tested for their veto activity in MLR cultures of C3H/Hej H-$2^k$ responder cells (host type) stimulated against irradiated splenocytes from Balb/c (donor type), or in an SJL culture (non-relevant control, H-$2^s$ type). The inhibition of killing activity exerted by the veto cells on the responder cells was determined 6 days post culturing by the $^{51}$Cr release assay.

Figure 2A:
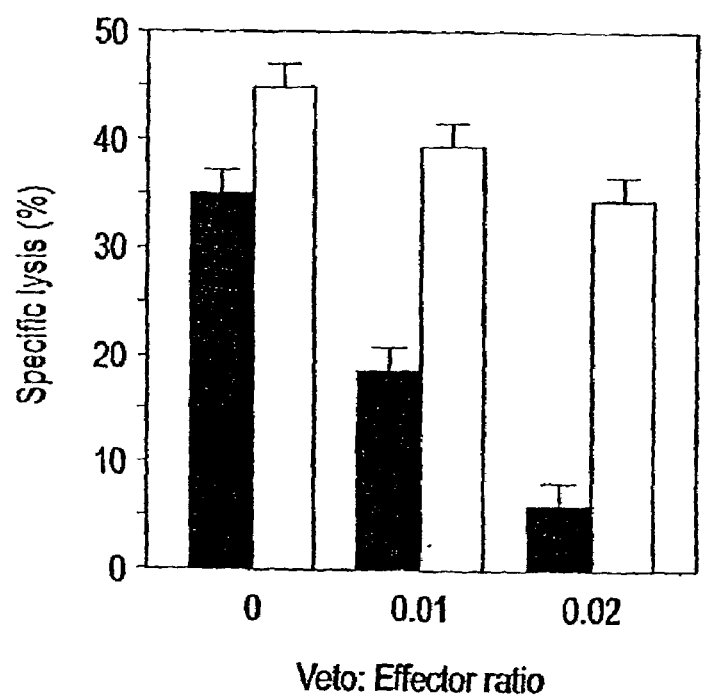
FIG. 2a is a histogram depicting the veto activity of non-alloreactive anti third-party CTLs. The Figure shows activity of anti-third party CTLs as a function of veto cell concentration as compiled from 17 different experiments. Specific lysis exhibited by responder cells (C3H/Hej) was documented upon stimulation against Balb/c (solid squares) or SJL (μopen squares) splenocytes, in the presence of different concentrations of cells from a Balb/c anti third-party (C57BL/6) CTL line.
Figure 3:
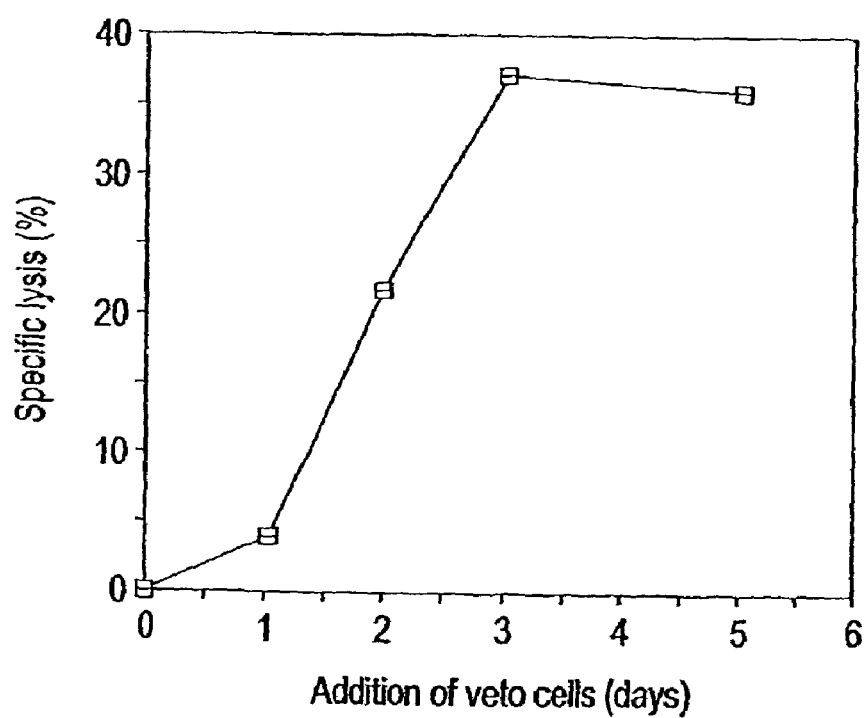
FIG. 3 is a graph depicting the veto activity of anti third party CTLs as a function of the time of veto cell addition. The percent killing of responder cells (C3H/Hej) stimulated against Balb/c splenocytes by a Balb/c anti third party (C57BL/6) CTL line (At a 1:50 veto responder cell ratio), was tested as a function of the time of CTL addition.

As can be seen in FIG. 2a (17 different experiments) and in FIG. 3 (one representative experiment), an addition of cells generated in a Balb/c CTL line directed against third party cells and cultured in the absence of IL-2, inhibits the killing activity of the responder cells (C3H/Hej) which were stimulated against Balb/c splenocytes. In contrast, the addition of cells from the same CTL line to responder cells (C3H/Hej) that were stimulated against SJL splenocytes, did not affect the responders killing activity. The specificity revealed by these results suggests that the non-alloreactive CTLs directed against third party, indeed possess veto activity.

Figure 2B:
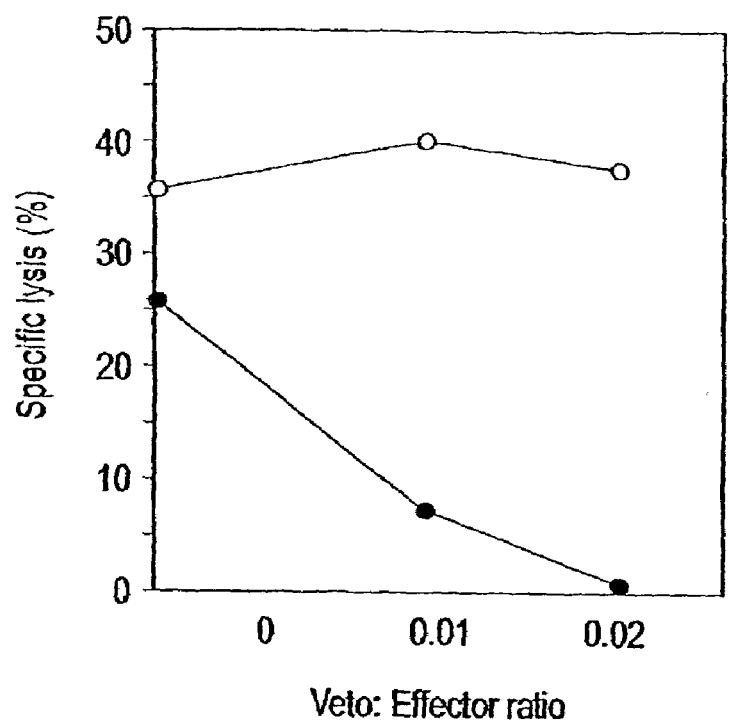
FIG. 2b is a graph depicting the veto effect of non-alloreactive anti third party CTLs as a function of effective veto/responder cell ratios. The killing of responder cells (CTL progenitors) (C3H/Hej) stimulated against Balb/c (solid circle) or SJL (open circle) splenocytes, was tested in the presence of different concentrations of cells from a Balb/c anti third party (C57BL/6) CTL line.

The dose response curve shown in FIG. 2b suggests that the anti-third party CTLs possess a very marked veto activity, attaining complete inhibition at a 1:50 veto/responder cell ratio. Addition of veto cells at 5 fold higher concentrations leads to non-specific elimination of CTL-p's directed at targets not sharing the donor type H-2 determinants (data not shown).

Optimal specific inhibition is achieved upon addition of anti-third party CTLs, (at a 1:50 veto/responder cell ratio), between day 0 and day 2. Thereafter, the veto effect is markedly reduced (FIG. 3). Thus, as previously suggested, veto cells probably inhibit or delete the responder cells at the precursor level[2]. Once these CTL precursors develop into differentiated CTLs the veto cells can no longer exert their effect.

Figure 4:
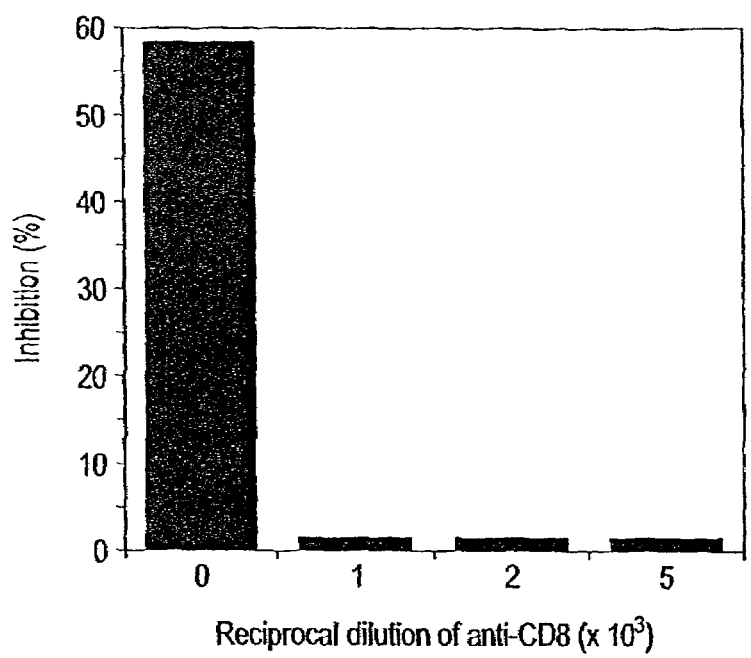
FIG. 4 is a histogram depicting the inhibition of the veto effect by a monoclonal anti-CD8 antibody. Anti-CD8 mAb (anti Ly-2.2) was added at different concentrations to mixed lymphocyte reaction (MLR) which consisted of responder cells (C3H/Hej) stimulated against Balb/c splenocytes, and cells from a Balb/c anti-third party (CS7BL/6) CTL line (At a 1:50 veto/responder cell ratio).

In addition, by using monoclonal antibodies directed against the CD8a Ly-2.2 allele expressed on the anti-third party CTLs but not on the responder cells, confirmed previous observations[18] that the CD8 molecules of the veto cells participate in the deletion of the responder cells (FIG. 4).

Figures 5A, 5B, 5C:
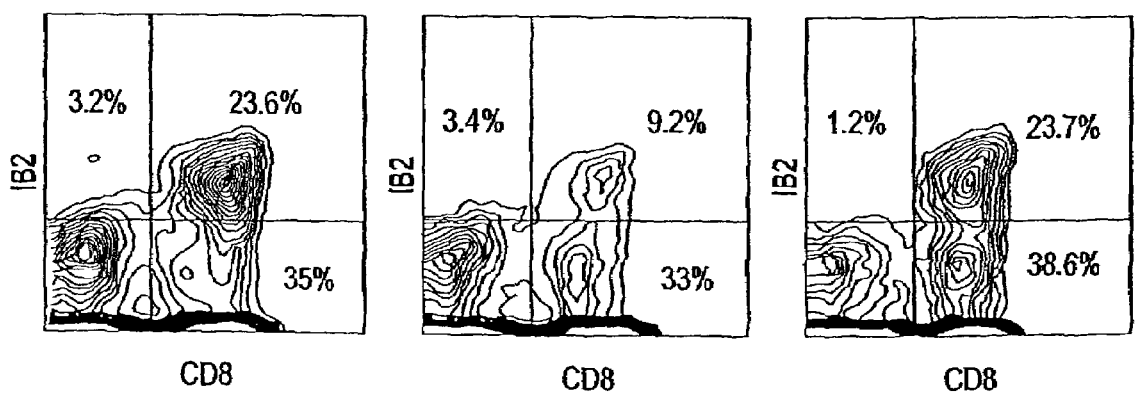
FIGS. 5a-c depict the specific deletion of responder CTL-p directed against the H-2 antigen of the veto cells. Splenocytes from 2c transgenic mice (H-2$^b$) bearing transgene TCR specific against H-2$^d$ (1B2$^+$) were stimulated in MLR against Balb/c splenocytes (H-2$^d$). The frequency of 1B2$^+$ CD8 T cells before (5a) and after addition to the MLR culture of Balb anti-C3H (5b) or SJL anti-C3H (Sc) CTLs, was determined by FACS 5 days after initiation of the MLR.

The role of Fas-Fas-L apoptosis: The role of apoptosis in responder cell deletion was confirmed by two approaches: (i) the addition of the apoptosis inhibitor (BD-FmK) to the MLR culture led to a complete inhibition of the veto effect (data not shown); and (ii) the addition of anti-third party CTLs of Balb/c (H-$2^d$) origin, to an MLR culture of TCR transgenic C57B1/6 responders bearing the 2C TCR directed against H-$2^d$, led to a marked and specific deletion of the transgenic responders upon stimulation against Balb/c stimulators (FIGS. 5a-c).

Considering that two distinct major apoptosis mechanisms, namely perforin mediated or Fas-Fas-L mediated apoptosis have been previously described, two different non-alloreactive anti-third party CTL lines from splenocytes of Fas-L deficient strain (C3H-gld, H-$2^k$) or from splenocytes of perforin deficient mice (PO, H-$2^{bd}$) were prepared. C3H-gld or PO-splenocytes were stimulated against irradiated C57BL/6 H-$2^b$ or DBA/1H-$2^q$ splenocytes, respectively, as described for wild type splenocytes (culturing for 10 days, without the addition of exogenous rhIL-2 during the first 4 days). The use of veto cells of gld -C3H/Hej (H-$2^k$ origin) and of PO (H-$2^{bd}$ origin) necessitated changes in the design of the MLR responders and stimulators utilized. Thus, the gld mutant anti-third party CTLs were added to bulk MLR cultures in which Balb/c responders were stimulated against C3H/Hej splenocytes. The PO knockout anti-third party CTLs were added to bulk MLR cultures in which C3H/Hej responders were stimulated against PO or SJL splenocytes.

Figure 6A:
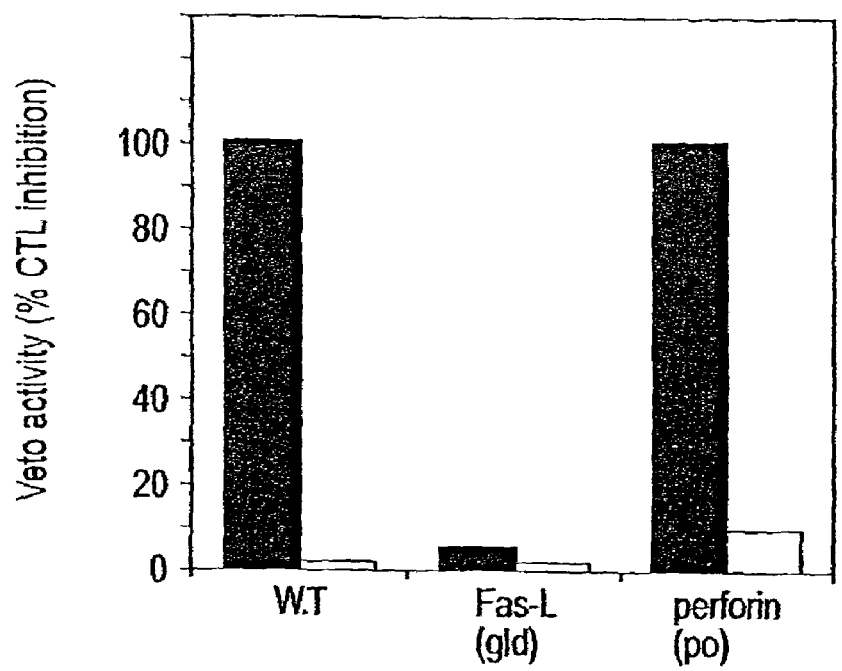
FIG. 6a is a histogram depicting the role of Fas ligand (Fas-L) and perforin in the veto activity of anti-third party CTLs. Anti-third party CTLs generated from wild type C3H splenocytes were compared to CTLs generated from Fas-L deficient gld/C3H or from perforin deficient PO splenocytes. Cultures for veto determination consisted of Balb anti-C3H MLR (solid column) while Balb anti-SJL served as a control for background inhibition (open column). In the case of PO CTLs, cultures for veto determination consisted of C3H anti-PO MLR (solid column) while C3H anti-SJL served as a control (open column).

As can be seen in FIG. 6a, the anti-third party CTLs originating from C3H-gld lacked veto activity, whereas the CTLs originating from perforin deficient mice did exhibit significant veto activity.

Figure 6B:
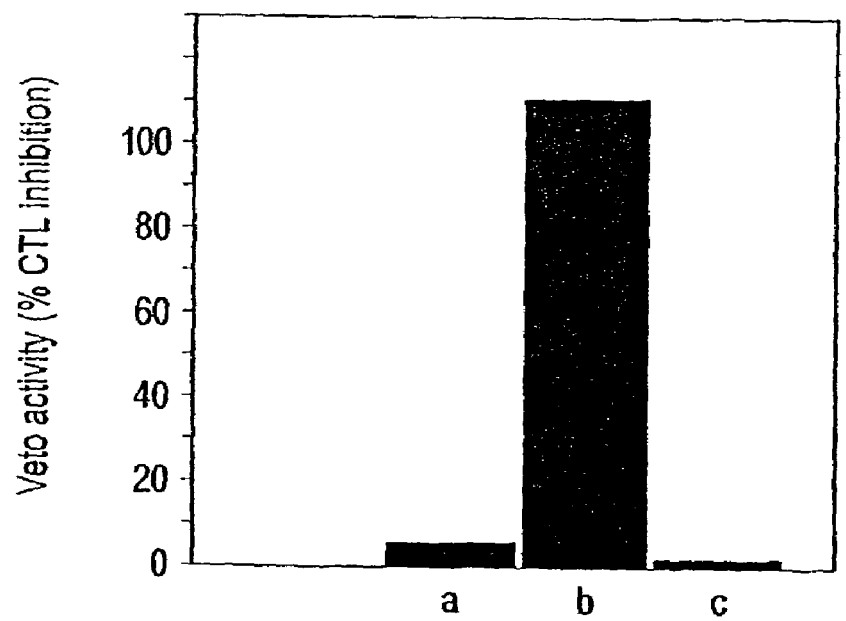
FIG. 6b is a histogram depicting the reversal of veto activity in Fas-L deficient CTLs by gene transfer of Fas-L. Anti third-party CTLs generated from wild type C3H splenocytes, were compared to CTLs generated from Fas-L deficient gld/C3H, before, a, and after transfection with Fas-L containing retroviral vector, b, or with a mock vector, c.

Additional evidence to the role of Fas-L in the veto effect was afforded by gene transfer experiments in which gld-anti-third party CTLs were transfected with Fas-L, using a retroviral vector. As can be seen in FIG. 6b such transfected CTLs exhibited marked veto activity compared to mock-infected anti-third party CTLs.

Figure 7A:
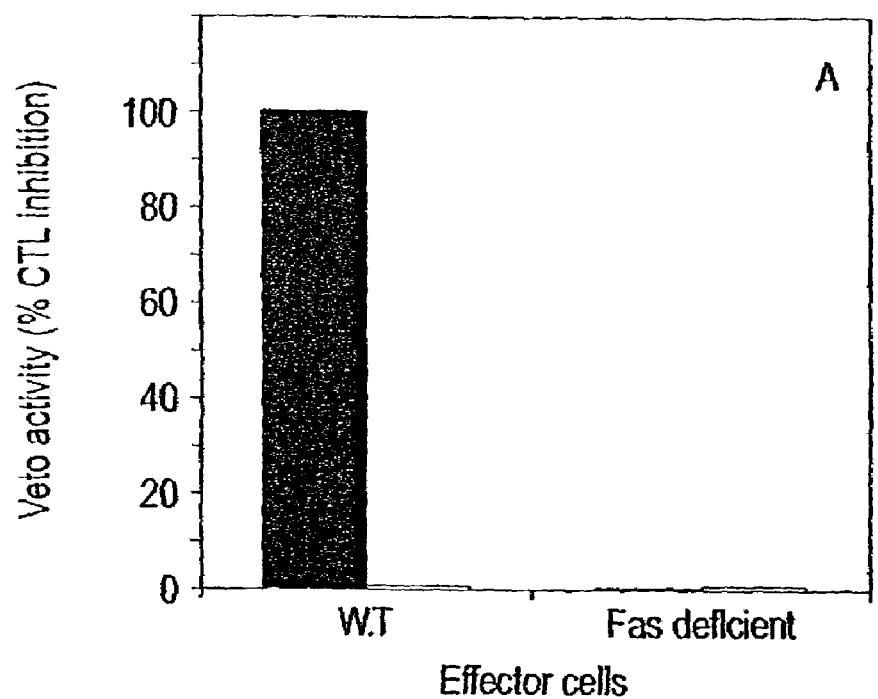
FIG. 7a is a histogram depicting the role of Fas in the veto activity of anti-third party CTLs. Responder CTL progenitors of wild type C3H or of Fas deficient lpr/C3H background, were compared for their sensitivity to the veto effect of Balb anti-C57BL/6 CTLs. Cultures for veto determination consisted of C3H anti-Balb MLR (solid columns) or lpr/C3H anti-SJL (open columns) which served as a control for determining background inhibition.
Figure 7B:
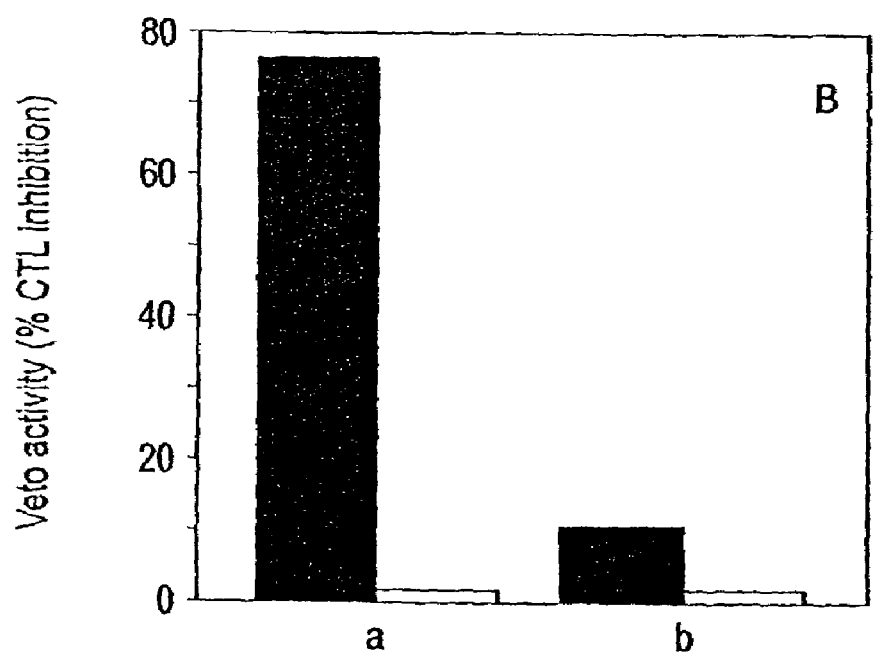
FIG. 7b is a histogram depicting the effect of a Fas-L antagonist on the veto effect of CTLs. Cultures for veto determination consisted of Balb anti-C3H MLR (solid columns) or Balb anti-SJL (open column) which served as a control for determining background inhibition.

Using a similar approach, the role of Fas in the veto activity induced by anti-third party CTLs was investigated. As can be seen in FIG. 7a, when Fas deficient C3H-lpr splenocytes were stimulated against Balb/c in the primary MLR culture, the addition of Balb/c anti-third party CTLs failed to inhibit the primary CTLs. In contrast, these cells exhibited veto activity when added to primary MLR cultures of wild type C3H responders. Similarly, a Fas antagonist (Fas fusion protein) also inhibited the veto effect of anti-third party CTLs (FIG. 7b).

FACS analysis of Fas during a typical MLR of 2C splenocytes against Balb/c stimulators (FIGS. 8a-d), revealed that Fas expression on CD8$^+$ 1B2$^+$ T-cells is markedly enhanced at 48 hr (FIG. 8b). Addition of Balb anti-C3H (FIG. 8c), but not SJL anti-C3H CTLs (FIG. 8d), led to a marked deletion of the Fas$^+$ activated CD8 T cells, illustrating the potent veto activity and the remarkable specificity by which the anti-third party veto CTLs expressing Fas-L [25, 29] are capable of selectively recognizing and killing Fas$^+$ T-cells aimed against their H-2 antigens.

Altogether these results suggest that the veto effect of non-alloreactive anti-third party CTLs is mediated by the simultaneous expression of CD8 and Fas-L on the veto CTLs and the expression of Fas on the effector CTL-p's directed against the antigens presented by the veto cells.

Example 2

Generation of Donor Anti-Third Party Human CTLs Depleted of Anti-Host CTL Precursors Following the demonstration described above that anti-third party CTLs can be depleted of anti-host CTLp an attempt to apply this approach to human settings has been undertaken. It will be appreciated in this respect, and it is well accepted among art scholars, that it is not at all predictable that an immunogenic approach effective in mice would have similar effectiveness in human beings.

Materials and Methods:

Establishment of anti-third party CTLs: Anti-third party CTLs were prepared by stimulating normal peripheral blood lymphocytes (PBL) s derived from a human donor against an Epstein-Barr virus (EBV) transformed cell line of known HLA type (hereinafter stimulator A). PBLs were cultured in growth complete medium+10% FCS (CM-RPMI 1640+2 mM L-glutamine+100 U/ml penicillin+0.1 mg/ml streptomycin+2 mM HEPES+1 mM sodium pyruvate+0.1 mM non-essential amino acids+$5\times10^{-5}$ M β-mercaptoethanol) at $2\times10^6$ cells/ml and were stimulated with $5\times10^4$ cells/ml irradiated (10,000 rad) stimulators.

Following 10 days of co-culture, the cells were harvested and live cells were isolated on Ficoll-Paque gradients and re-stimulated, $5\times10^6$ cells/ml with $1.5\times10^5$ cells/ml of stimulators. Four days later the cultures were treated with hrIL-2 at 20 U/ml, for the first time.

Thereafter, the cultures were treated three times per week, each time with 20 U/ml rhIL-2. The third treatment also included the addition of irradiated stimulators at a ratio of 4:1.

The CTL line, originally stimulated against stimulator S was tested for CTL-p responders against the original stimulator S or against stimulator No. 38 which represents the intended host.

The cells from this anti-third party CTL line were cultured either with stimulator S or with stimulator 38, at $1\times10^6$ cell/ml 1:1 for 5 days. The cells were then harvested from the bulk culture and serial dilutions of CTL responder cells ($4\times10^4$ to $0.2\times10^3$) per well, were prepared with the original irradiated stimulators. Each well contains $10^5$ of irradiated (30 Gy) stimulator 38 or $3\times10^4$ (100 Gy) irradiated stimulator S. The cultures were incubated for 7 days in complete medium+1%+20 U/ml rhIL-2.

Cytotoxicity was assayed with $5\times10^3$ $^{51}$Cr labeled blasts (target cells) from S, No. 38 and No. 40 (control for non-specific killing) donors.

Normal unseparated PBLs from the original donor of the cell line were tested in parallel.

Figure 10:
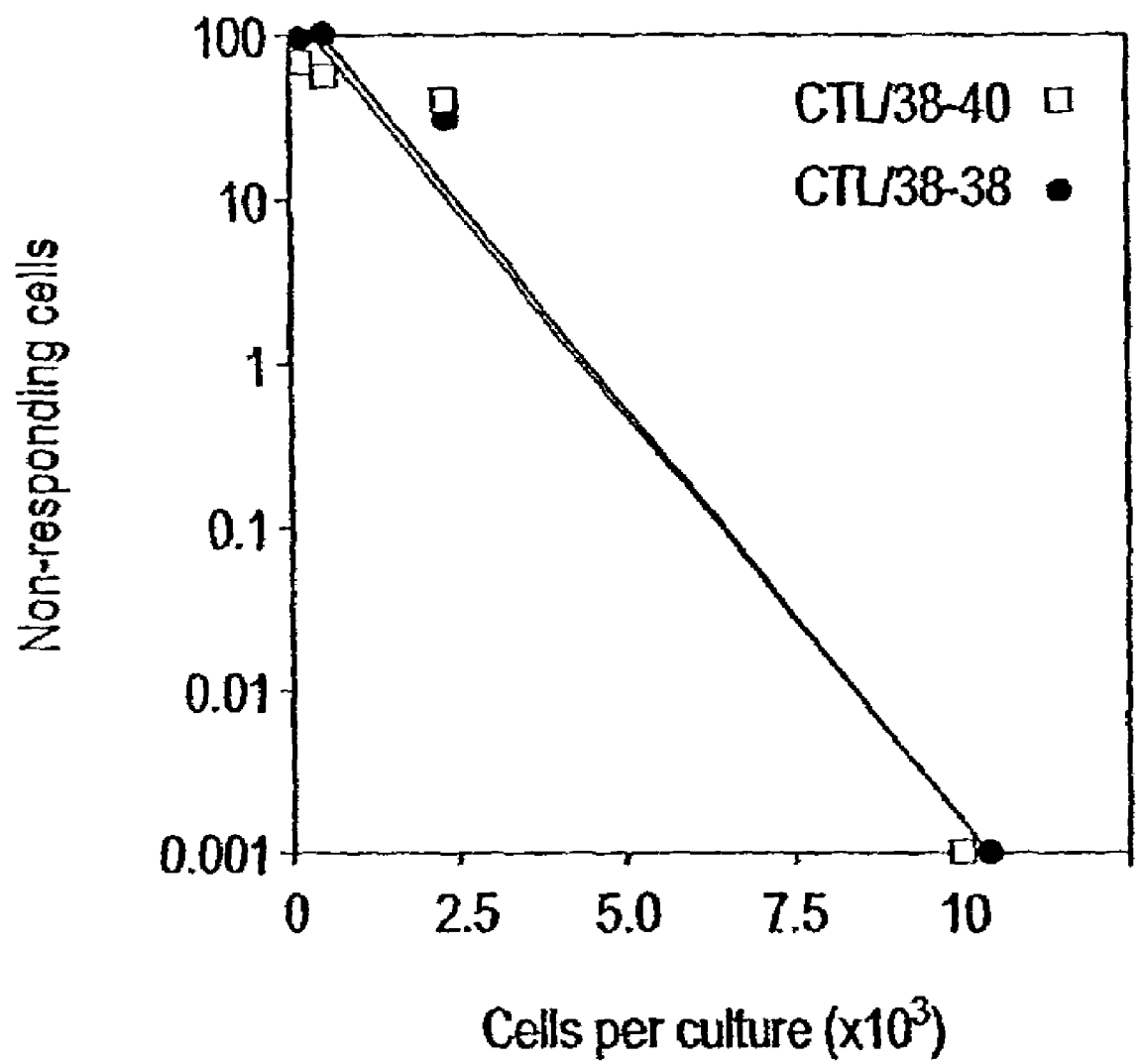
FIG. 10 is a graph depicting the relationship between cells per culture and the percent of non-responding cells of a CTL line established from PBL of donor R (described in FIG. 1) by stimulation against third party EBV transformed stimulators (named S). When stimulating the cells of this CTL line against the host type PBL (patient No. 38), the specific killing was demonstrated to be negligible (circle) as is compared to that found against control cells (patient No. 40, non-specific background) (square).

Experimental Results:

Non-alloreactive human CTL lines were established in-vitro by stimulating PBLs with EBV transformed cell line of known HLA type. While a significant level of anti-host CTLp was demonstrated in untreated PBL of donor A (FIG. 9), it was found that the anti-third party CTL line that was generated from PBL of the same donor A was markedly depleted of such cells (FIG. 10). These results indicate that the CTL preparation of this Example is depleted of T-cells having the potential of maturing into anti-host CTLs (alloreactive CTLs) and is therefore advantageous as an agents for enhancing graft acceptance in humans.

Conclusions

Prior art approaches, which make use of T-cell stimulation with the very antigens against which tolerance is desired, might involve some risk for generating committed CTLs, if any of the CTL-p escape deletion or anergy induction. Once such anti-host CTLs are generated, it is very difficult to suppress their alloreactivity in vivo.

A more recent approach, demonstrated that a "megadose" of cells can be applied to induce tolerance in sublethally irradiated mice, and as such effectively overcome the marked resistance presented by the large number of lymphocytes surviving the sublethal conditioning. However, the number of cells required to attain this desirable goal may not be easily collected from human donors.

Non-alloreactive anti-third party CTLs which can be used to enhance graft acceptance in mice were also shown, however, it was soon realized that such CTL preparations are not depleted of T-cells capable of developing post transplantation into anti-host CTLs inflicting GVHD.

The present research demonstrates that donor anti-third party CTLs can be depleted of anti-host alloreactivity if exogenous IL-2 is not provided during the initial days of the bulk culture with the stimulator cells. Such non-alloreactive CTLs can enhance engraftment, without GVHD, of, for example, T-cell depleted BM originating from the same donor.

The present study further uncovers the mechanism responsible for the marked potent veto activity of such anti-third party CTLs.

By utilizing anti-CD8 antibodies, the present study demonstrates that the expression of CD8 on the CTLs is crucial for CTL-p recognition.

By using anti-third party non-alloreactive CTLs generated from spleen cells of different mutant mice the present study demonstrates that the veto activity of these cells is mediated by apoptosis via the Fas-Fas-L system and not by the perforin mechanism.

Thus, the results of the present study suggest that simultaneous expression of both CD8 and Fas-L on the CTL surface and the expression of Fas on the effector CTL-p is a prerequisite for the veto activity.

Example 3

The Primate Model

Materials and Methods:

Monkeys: Female cynomolgus monkeys (aged 1.5-2 years) weighing 1.5-2.5 kg, are used as bone marrow recipients and MLC mismatched male cynomolgus monkeys weighing 6-9 kg are used as donors.

Conditioning regimen: A sublethal irradiation-based protocol utilized is as follows: Fludarabine (FLU) 40 mg/m$^2$ from day-9 (prior to transplantation) to day-5 (total amount 200 mg/m$^2$); Rabbit anti-thymocyte globulin (ATG) 5 mg/kg from day-7 to -3 and 6.5 or 7 Gy TBI (dose rate 0.15 Gy/min) delivered on day-1.

Peripheral blood mononuclear cells collection: RhG-CSF (20 mg/kg/day) is administered to donor monkeys over a period of five days in two daily subcutaneous injections. Two leukapheresis procedures are performed between days 4 and 5.

Donors and leukapheresis: Healthy male cynomologus donors are subjected to a double or triple set of 100-minute leukapheresis on a Cobe Spectra cell separator, as described by Hillyer et al. [reference No. 27] with the following minor modifications: acid, citrate, dextrose (ACD)-to-blood ratio is 12:14 and centrifuge speed is 1,600 rpm.

Peripheral blood mononuclear cell processing: Peripheral blood progenitor cells (PBPC) preparations are depleted of T-lymphocytes using the E-rosetting technique, as previously described[26]. Stem cells are then purified by positive selection by using an avidin-biotin immunoadsorbtion column (CEPRATE SC System, CellPro, Bothell, Wash.), according to the manufacturer's instructions. The number of CD34+ cells is measured both in whole blood and in the leukapheresis product by flow cytometry. The T-lymphocytes before and after T-cell-depletion are also measured, by using a phycoerythrin-coupled anti-CD2 monoclonal antibody. Aliquots are taken for differential cell counts, mAb staining and GFU-GM assay at each stage of processing.

Supportive care: Monkeys are cared for in laminar airflow cages until the neutrophils count recovered to $1\times10^9$/L. All monkeys receive cyproxin and amphotericin B as gut preparation, combined antibiotics as prophylaxis against bacterial infection since the day of transplant, and fluconazole as antifingal prophylaxis. Acyclovir is administered for preventing viral infection. Whole blood or component blood products are transfused according to monkey's hematocrit and platelet count. All blood products are irradiated with 25-30 Gy and filtered before transfusion.

Engraftment and chimerism deteriniation: Time to engraftment is assessed by determining the day after transplant on which monkeys displayed a level of 0.5 neutrophils$\times10^9$/L and $25\times10^9$ platelets/L independent of transfusion support. Chimerism is assessed by quantitative polymerase chain reaction (PCR). Briefly, the PCR products are subjected to 3% MetaPhor agarose (FMC) gel. The density of each band for Y specific DNA and competitor DNA is measured by using computerized densitometer and the target (Y specific)/competitor DNA (T/C) ratio for each sample is calculated. At the point where Y specific and competitor DNA are in equivalence (i.e., ratio=1.0), the starting amount of Y specific DNA prior to PCR is equal to the known starting amount of competitor DNA.

Generation of donor-anti-third party CTLs: A slightly modified procedure is used for preparation of monkey donor anti-third party CTLs. Peripheral blood cells of donor and third party monkeys are fractionated on Ficoll-Paque plus and the isolated mononuclear cells, $1\times10^6$/ml of responder cells and $2\times10^6$/ml irradiated (20 Gy) third party stimulators, are cultured for 10 days in CTCM medium. Four days hours after seeding, human rhIL-2 (20 U/ml, Eurocetus, Milan, Italy), is added every 24 hours.

Example 4

Preparation of Human CD8+ CTLs is Enhanced by Removal of CD4+ and CD56+ Cells

Figure 11A:
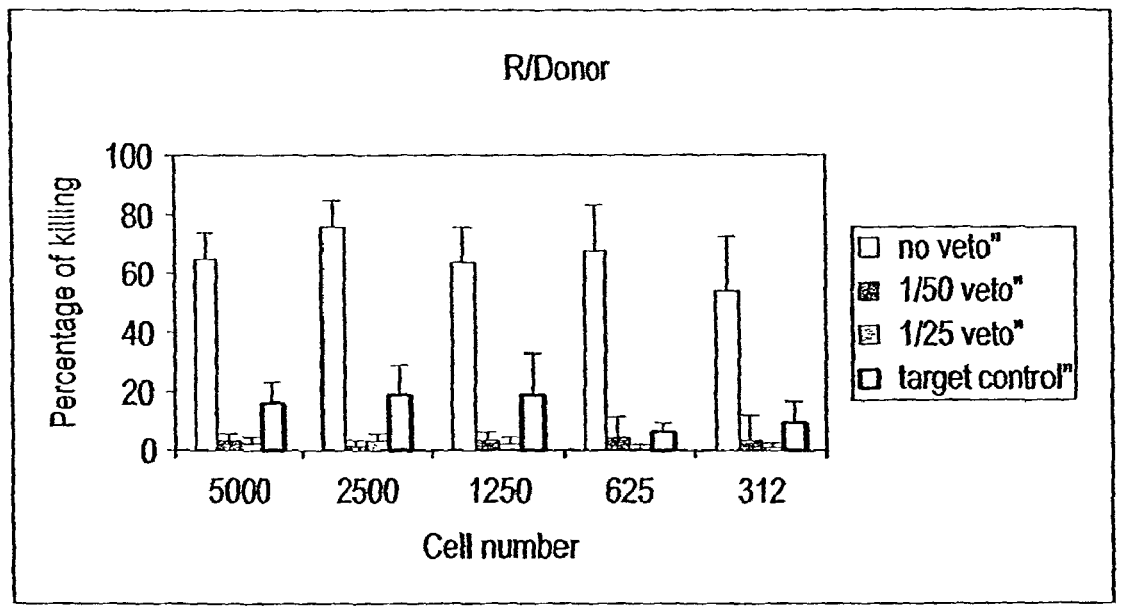
FIGS. 11a-b are bar graphs demonstrating the veto activity of human anti-third party CTLs.
Figure 11B:
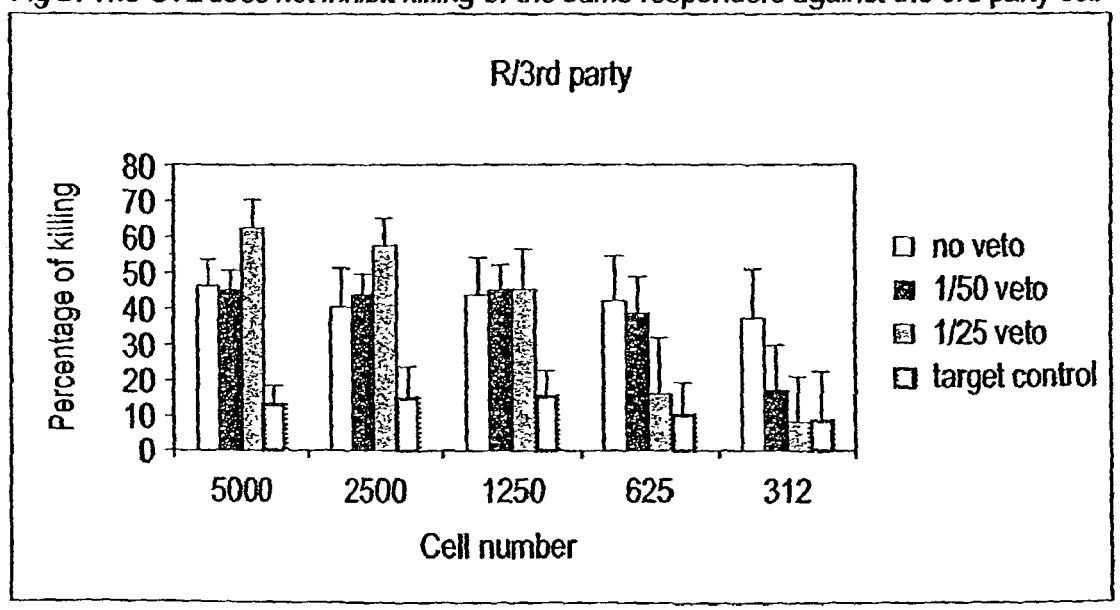

It was observed that the level of CD8+ cells in the CTL cultures prepared essentially as described above is extremely variable. Therefore, selection of CD8+ cells by removal (negative selection) of CD4+ and CD56+ cells, using antibodies linked to magnetic beads. As can be seen in FIGS. 11a-b the cells obtained by this procedure exhibited very potent veto activity at a ratio of 1:25 and 1:50 veto to effector cell ratio.

Treatment of donor cells: Anti third party CTLs were prepared by stimulating donor peripheral blood lymphocytes against EBV transformed human derived cell line of a known HLA type (stimulators) in 24—well plates. The peripheral blood lymphocytes were cultured in growth complete medium supplemented with 10% fetal calf serum (CM-RPMI 1640, 2 mM L-glutamine, 100 Units/ml penicillin, 0.1 mg/ml streptomycin, 2 mM Hepes, 1 mM sodium pyruvate, 0.1 mM non essential amino acids, $5\times10^{-5}$ M β2-mercaptoethanol) at $1\times10^6$ cells/ml and stimulated with $2.5\times10^4$ cells/ml irradiated (10,000 Rad) stimulators, in 250 ml flasks at a volume of 50 ml.

After 10 days of co-culture, the cells were harvested and live cells were isolated on ficoll gradient and re-stimulated, the cells were resuspended to a concentration of $5\times10^5$ cells/ml and were re-stimulated with $1.5\times10^5$ stimulator cells/ml.

Four days later, the cells were negatively selected for CD4+ and CD56+ cells with MACS beads (Miltenyi Biotec). The unbound cells were resuspended at $1\times10^6$ cells/ml and re-stimulated with $0.33\times10^6$ stimulator cells/ml. At this stage (following two weeks in culture) the cells were treated with interieukin-2 (IL-2, Proleukin) at 600 Units/ml.

Thereafter, the cultures were treated three times per week, each time with 600U/ml IL-2. The third time also included the addition of irradiated stimulators at a ratio of 4:1. Please note that during the first two weeks of culture, no IL-2 was added to the cells.

Example 5

Experiments in Human—Case Report

Treatment of donor cells: Anti third party CTLs were prepared by stimulating donor peripheral blood lymphocytes against EBV transformed human derived cell line of a known HLA type (stimulators), as described in Example 4 above. The CTLs obtained were infused to a patient as described bellow in order to tolerize the immune system of the patient, so as to facilitate engraftment of stem cells thereto.

The patient was diagnosed on May 1998 with mantle cell lymphoma The patient was treated with 4 courses of PRO-MACE resulting in partial remission. During December 1998 the patient was treated with a high dose of Cytoxan (CTX) and autologous peripheral blood stem cells were harvested and cryopreserved. During March 1999 the patient received an autologous transplant after conditioning with TBI-and thiotepa. Thereafter, complete remission has been achieved.

During October 1999 the patient relapsed with lymphoplasmacytoid infiltration of the bone marrow. IgG/k serum levels were treated by plasmapheresis and dexametasone until July 2000.

During October 2000 the patient received an allogeneic mega dose stem cell transplant from a mis-matched haploidentical child. The patient was coditioned with melphalan 70 mg/sqm on day −12, thiotepa 7 mg/kg body weight on day −11, fludarabin 40 mg/sqm from day −9 to day −6, Fresenius ATG 2.5 mg/kg body weight from day −9 to day −6. On day the −1, the anti-third party CTLs were infused at a cell dose of $6.1\times10^6$ CTL/Kg recipient body weight. On day 0 the donor stem cells were infused at a dose of $9.7\times10^6$ CD34+ cells per Kg body weight (processed by CliniMACS and including 40,000 CD3T cells/Kg body weight). Conditioning as well as CTL infusion was well tolerated despite the pre-transplant cardio-pulnonary compromission of this old patient.

Neutrophil engraftment (500/mm$^3$) was first found on day +8, 980/mm$^3$ on day +11 , 2,760/mm$^3$ on day +14, and 5,370/mm$^3$ on day +21.

Platelet reconstitution (35,000/mm³) was first achieved on day +18.

CMV antigenemia became positive (only 4 cells) on day +40 (Patient was not under prophylactic treatment).

Gammapathy on electrophoresis, typical of Lymphoma patients, was reduced to normal levels (before transplant—33.8%, 21% on day +20 post transplant).

IgG level was reduced to normal levels (before transplant—2330 mg/dl, 1550 mg/dl post transplant).

FISH analysis on day +20 post transplant revealed that all the cells in the peripheral blood and in the bone marrow were of donor origin.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications cited herein are incorporated by reference in their entirety.

REFERENCES

1. Bachar-Lustig E, Li H W, Gur H, Krauthgamer R, Marcus H, Reisner Y: Induction of donor-type chimerism and transplantation tolerance across major histocompatibility barriers in sublethally irradiated mice by sca-1(+)Lin(−) bone marrow progenitor cells: synergism with non-alloreactive (Host×Donor)F(1) T cells [In Process Citation]. Blood 94:3212, 1999.

2. Miller R G: An immunological suppressor cell inactivating cytotoxic T-lymphocyte precursor cells recognizing it. Nature 287:544, 1980.

3. Lapidot T, Faktorowich Y, Lubin I, Reisner Y: Enhancement of T cell-depleted bone marrow allografts in the absence of graft-versus-host disease is mediated by CD8⁺ CD4⁻ and not by CD8⁻CD4⁺ thyrnocytes. Blood 80:2406, 1992.

4. Kaufman C L, Colson Y L, Wren S M, Watkins S. Simmons R L, Ildstad S T: Phenotypic characterization of a novel bone marrow-derived cell that facilitates engraftment of allogeneic bone marrow stem cells. Blood 84:2436, 1994.

5. Pierce G E, Watts L M: Do donor cells function as veto cells in the induction and maintenance of tolerance across an MHC disparity in mixed lymphoid radiation chimeras? Transplantation 55:882, 1993

6. Cobbold S P, Martin G, Qin S, Waldmann H: Monoclonal antibodies to promote marrow engraftment and tissue graft tolerance. Nature 323:164 1986.

7. Kikuya S, Inaba M, Ogata H, Yasumizu R, Inaba K: Wheat germ agglutinin-positive cells in a stem cell-enriched fraction of mouse bone marrow have potent natural suppressor activity. Proc Natl Acad Sci USA 85:4824, 1988.

8. Kiyoshi H, Hiruma K, Nakamura H, Henkart P, Gress R: Clonal deletion of postthymic T cells: Veto cells kill precursor cytotoxic T lymphocytes. J Exp Med 175:863, 1992.

9. Pierce G E, Watts L M: Thy 1+ donor cells function as veto cells in the maintenance of tolerance across a major histocompatibility complex disparity in mixed-lymphoid radiation chimeras. Transplant Proc 25:331, 1993.

10. Strober S, Palathumpat V, Schwadron R, Hertel-Wulff B: Cloned natural suppressor cells prevent lethal graft-vs-host disease. J Immunol 138:699, 1987.

11. Tschering T, Claesson M: Veto-like down regulation of T helper cell reactivity in vivo by injection of semi-allogeneic spleen cells. Immunology Letters 29:223, 1991.

12. Cassell D J, Forman J: Regulation of the cytotoxic T lymphocyte response against Qa-1 alloantigens. J Immunol 144:4075, 1990.

13. Claesson M H, Ropke C: Antiself suppressive (veto) activity of responder cells in mixed lymphocyte cultures. Curr Top Microbiol Immunol 126:213, 1986.

14. Fink P J, Rammensee H G, Bevan M J: Cloned cytolyfic T cells can suppress primary cytotoxic responses directed against them. J Immunol 133:1775, 1984

15. Fink P J, Shimonkevitz R P, Bevan M J: Veto cells. Annu Rev Immunol 6:115, 1988.

16. Tscherning T, Claesson M H: Veto suppression: the peripheral way of T cell tolerization. Exp Clin Immunogenet 10:179, 1993.

17. Claesson M H: Veto cell H-2 antigens: veto cell activity is restricted by determinants encoded by K, D, and I MHC regions. Cell Immunol 109:360, 1987.

18. Sambhara S R, Miller R G: Programmed cell death of T cells signaled by the T cell receptor and the alpha 3 domain of class I MHC. Science 252:1424, 1991.

19. Sambhara S R, Miller R G: Reduction of CTL antipeptide response mediated by CD8+ cells whose class I MHC can bind the peptide. J Immunol 152:1103, 1994.

20. Hiruma K, Nakamura H, Henkart P A, Gress R E: Clonal deletion of postthymic T cells: veto cells kill precursor cytotoxic T lymphocytes. J Exp Med 175:863, 1992.

21. Qi Y, Berg R, Singleton M A, Debrick J E, Staerz U D: Hybrid antibody mediated veto of cytotoxic T lymphocyte responses. J Exp Med 183:1973, 1996.

22. Asiedu C M Y, Wang W, Huang Z, Contreras J, George J F, Thomas J M: Immunoregulatory role of CD8a in the veto effect. Transforming growth factor-b1 activation. Transplantation 67:372, 1999.

23. George J F, Thomas J M: The molecular mechanisms of veto mediated regulation of alloresponsiveness [In Process Citation]. J Mol Med 77:519, 1999.

24. Reisner Y, Li H W, Krauthgamer R, Marcus H, Bachar-Lustig E: Non-alloreactive donor anti-third party CTL's facilititate BM allograft across major histicompatibility barriers in sublethally irradiated mice. Blood 92:265a, 1998.

25. Reich-Zeliger S, Bachar-Lustig E, Zhao Y, Reisner Y: Enhancement of BM allografts by non-alloreactive donor CTL's: CD8 binding and Fas-FasL apoptosis mediate the veto effect. blood 94:605a, 1999.

26. Aversa F, Tabilio A, Velardi A, Cunningham I, Terenzi A, Falzetti F, Ruggeri L, Barbabietola G, Aristei C, Latini P, Reisner Y, Martelli M F: Transplantation of high-risk acute leukemia with T-cell-depleted stem cells from related donor with one fully mismatched HLA baplotype. N Eng J Med 339:1186, 1998.

27. Hillyer C D, Swenson R B, Harp K K, Lackey D A, Winton E F: Peripheral blood stem cell acquisition by large-volume leukapheresis in growth factor-stimulated and unstimulated rhesus monkey: Development of an model. Exp Hematol 21:1455, 1993.

28. Bachar-Lustig E, Kestel A, Krauhgamer R, Gan J, Reisner Y: Murine and human non-alloreactive anti-3$^{rd}$ party CTL: a novel facilitating cell with maredly reduced GVH reactivity. Blood: 96 No 11, 3739 (Abstract No 1610), 2000

29. Reich-Zeliger S, Zhao Y, Krauthgamer R, Bachar-Lustig E, Reisner Y, Anti-third party CD8+ CTLs as potent veto cells: Coexpression of CD8 and FasL is a prerequisite. Immunity, 13:507, 2000.

What is claimed is:

1. A method of preventing or decreasing graft rejection in a human recipient of a transplant which is derived from a donor which is allogeneic with respect to the recipient, the method comprising:
   (a) conditioning the recipient under lethal or sublethal conditions;
   (b) transplanting the transplant into the recipient; and
   (c) administering to the recipient a dose of a cell preparation, wherein said cell preparation comprises non-alloreactive anti-third party cytotoxic T-lymphocytes (CTLs), does not comprise lymphocytes capable of developing into anti-recipient CTLs, and does not substantially comprise CD4+ cells and/or CD56+ cells, and wherein said cell preparation is generated by a method which comprises:
      (i) directing peripheral blood lymphocytes derived from the donor against a third party antigen or antigens, wherein said third party antigen or antigens are allogeneic cells, thereby generating third party antigen-treated lymphocytes which comprise anti-third party CTLs;
      (ii) substantially depleting said peripheral blood lymphocytes derived from the donor of CD4+ cells and/or CD56+ cells; and
      (iii) substantially depleting, by deprivation of exogenous IL-2, said third party antigen-treated lymphocytes of T-lymphocytes capable of developing into anti-recipient CTLs, thereby preventing or decreasing graft rejection in the recipient of the transplant.

2. The method of claim 1, wherein said cell preparation is substantially depleted of CD56+ cells or CD4+ cells.

3. The method of claim 1, wherein the donor is HLA identical with respect to the recipient.

4. The method of claim 1, wherein the transplant is selected from the group consisting of cells, a tissue and an organ.

5. The method of claim 1, wherein said third party allogenic cells have HLA antigens which are different from HLA antigens of the donor but which are not cross reactive with HLA antigens of the recipient.

6. The method of claim 1, wherein said third party allogenic cells are stimulatory cells selected from the group consisting of cells purified from peripheral blood lymphocytes, cells purified from spleen, cells purified from lymph nodes, cytokine-mobilized PBLs and in vitro expanded antigen-presenting cells (APC).

7. The method of claim 1, wherein steps (a) and (b) are effected at the same time.

8. The method of claim 1, wherein step (a) is effected following step (b).

9. A method of treating a human recipient suffering from a disease requiring immature hematopoietic cell transplantation, the method comprising:
   (a) conditioning the recipient under lethal or sublethal conditions;
   (b) administering to the recipient a dose which comprises immature hematopoietic cells derived from a donor which is allogeneic with respect to the recipient; and
   (c) administering to the recipient a dose of a cell preparation which comprises non-alloreactive anti-third party cytotoxic T-lymphocytes (CTLs), does not comprise T lymphocytes capable of developing into anti-recipient CTLs, does not substantially comprise CD4+ cells and/or CD56+ cells, and is generated by a method which comprises:
      (i) directing peripheral blood lymphocytes derived from the donor against a third party antigen or antigens, wherein said third party antigen or antigens are allogeneic cells, thereby generating third party antigen-treated lymphocytes which comprise anti-third party CTLs;
      (ii) substantially depleting said peripheral blood lymphocytes derived from the donor of CD4+ cells and/or CD56+ cells; and
      (iii) substantially depleting, by deprivation of exogenous IL-2, said third party antigen-treated lymphocytes of T-lymphocytes capable of developing into anti-recipient CTLs, thereby preventing or treating the recipient suffering from the disease requiring immature hematopoietic cell transplantation.

10. The method of claim 9, wherein said cell preparation is substantially depleted of CD56+ cells or CD4+ cells.

11. The method of claim 9, wherein said donor is HLA non-identical with respect to the recipient.

12. The method of claim 9, wherein said third party allogenic cells have HLA antigens which are different from HLA antigens of said donor and which are not cross reactive with HLA antigens of the recipient.

13. The method of claim 9, wherein said third party allogenic cells are stimulatory cells selected from the group consisting of cells purified from peripheral blood lymphocytes, cells purified from spleen, cells purified from lymph nodes, cytokine-mobilized PBLs and in vitro expanded antigen-presenting cells (APC).

14. The method of claim 9, wherein said immature hematopoietic cells are cells which are derived from a source selected from the group consisting of bone marrow, mobilized peripheral blood, fetal liver, yolk sac and/or cord blood.

15. The method of claim 14, wherein said cells which are derived from mobilized peripheral blood are obtained by leukapheresis of peripheral blood of said donor after stimulation of said donor with a suitable cytokine.

16. The method of claim 9, wherein said immature hematopoietic cells are T-cell depleted hematopoietic progenitor cells.

17. The method of claim 9, wherein said immature hematopoietic cells are CD34+ cells.

18. The method of claim 9, wherein a cell ratio between said cytotoxic T-lymphocytes and said immature hematopoietic cells is at least 1 to 100.

19. The method of claim 9, wherein steps (b) and (c) are effected at the same time.

20. The method of claim 9, wherein step (b) is effected following step (c).

21. A method of producing a cell preparation for preventing or decreasing graft rejection in a human recipient of a transplant, wherein the recipient is conditioned under sublethal conditions, wherein the transplant is derived from a donor which is allogeneic with respect to the recipient, wherein the cell preparation comprises non-alloreactive anti-third party cytotoxic T-lymphocytes (CTLs), wherein the cell preparation does not comprises T-lymphocytes capable of developing into anti-recipient CTLs, and wherein the cell preparation does not comprise CD4+ cells and/or CD56+ cells, the method comprising:
   (i) directing peripheral blood lymphocytes derived from the donor against a third party antigen or antigens, wherein said third party antigen or antigens are allogeneic cells, thereby generating third party antigen-treated lymphocytes which comprise anti-third party CTLs;

(ii) substantially depleting, by deprivation of exogenous IL-2, said third party antigen-treated lymphocytes of T-lymphocytes capable of developing into anti-recipient CTLs; and (iii) removing CD4+ cells and/or CD56+ cells from said peripheral blood lymphocytes derived from the donor, thereby producing the cell preparation.

22. The method of claim 21, wherein step (iii) is effected by removing both the CD56+ cells and the CD4+ cells from said peripheral blood lymphocytes derived from the donor.

23. The method of claim 21, wherein said third party allogenic cells have HLA antigens which are different from HLA antigens of the donor and which are not cross reactive with HLA antigens of the recipient.

24. The method of claim 21, wherein said third party allogenic cells are stimulatory cells selected from the group consisting of cells purified from peripheral blood lymphocytes, cells purified from spleen, cells purified from lymph nodes, cytokine-mobilized PBLs and in vitro expanded antigen-presenting cells (APC).

25. A cell preparation for preventing or decreasing graft rejection in a human recipient of a transplant, wherein the recipient has been conditioned under lethal or sublethal conditions, wherein the transplant is derived from a donor which is allogeneic with respect to the recipient, wherein the cell preparation comprises non-alloreactive anti-third party cytotoxic T-lymphocytes (CTLs), the cell preparation comprising donor derived non-alloreactive anti-third party cytotoxic T-lymphocytes (CTLs), and wherein the cell preparation does not comprise T-lymphocytes capable of developing into anti-recipient CTLs and does not comprise CD4+ cells and/or CD56+ cells; the cell preparation having been generated by a method which comprises: directing peripheral blood lymphocytes derived from the donor against a third party antigen or antigens, wherein said third party antigen or antigens are allogeneic cells, thereby generating third party antigen-treated lymphocytes which comprise anti-third party CTLs; depleting said peripheral blood lymphocytes derived from the donor of CD4+ cells and/or CD56+ cells; and substantially depleting, by deprivation of exogenous IL-2, said third party antigen-treated lymphocytes of T-lymphocytes capable of developing into anti-recipient CTLs.

26. The cell preparation of claim 25, wherein the cell preparation does not comprise CD56+ cells or CD4+ cells.

27. The cell preparation of claim 25, wherein said third party allogenic cells have HLA antigens which are different from HLA antigens of the donor and which are not cross reactive with HLA antigens of the recipient.

28. The cell preparation of claim 25, wherein said third party allogenic cells are stimulatory cells selected from the group consisting of cells purified from peripheral blood lymphocytes, cells purified from spleen, cells purified from lymph nodes, cytokine-mobilized PBLs and in vitro expanded antigen-presenting cells (APC).

29. The cell preparation of claim 25, wherein the cell preparation further comprises immature hematopoietic cells derived from the donor.

30. The cell preparation of claim 29, wherein said immature hematopoietic cells are derived from a source selected from the group consisting of bone marrow, mobilized peripheral blood, fetal liver, yolk sac and cord blood.

31. The cell preparation of claim 30, wherein said cells derived from mobilized peripheral blood are obtained by leukapheresis of peripheral blood of the donor after stimulation of the donor with a suitable cytokine.

32. The cell preparation of claim 29, wherein said immature hematopoietic cells are T-cell depleted hematopoietic progenitor cells.

33. The cell preparation of claim 29, wherein said immature hematopoietic cells are CD34+ cells.

34. The cell preparation of claim 29, wherein a cell ratio between said cytotoxic T-lymphocytes and said immature hematopoietic cells including stem cells is at least 1 to 100.

35. The method of claim 1, wherein the transplant comprises immature hematopoietic cells.

36. The method of claim 35, wherein said immature hematopoietic cells are CD34+ cells.

37. The method of claim 35, wherein said immature hematopoietic cells are stem cells.

38. The method-of claim 1, wherein the donor is HLA non-identical with respect to the recipient.

39. The method-of claim 1, wherein the donor is mismatched haploidentical with respect to the recipient.

40. The method of claim 1, wherein step (a) is effected following step (b).

41. The method of claim 1, wherein step (a) is effected prior to step (b).

42. The method of claim 35, wherein the recipient has a malignant disease.

43. The method of claim 35, wherein the recipient has a hematopoietic malignant disease.

44. The method of claim 35, wherein the recipient has a lymphoma.

45. The method of claim 9, wherein said immature hematopoietic cells are stem cells.

46. The method-of claim 9, wherein said donor is mismatched haploidentical with respect to the recipient.

47. The method of claim 9, wherein step (b) is effected following step (c).

48. The method of claim 9, wherein the disease is a malignant disease.

49. The method of claim 9, wherein the disease is a hematopoietic malignancy.

50. The method of claim 9, wherein the disease is a lymphoma.

51. The cell preparation of claim 29, wherein said immature hematopoietic cells are stem cells.

52. A method of producing a cell preparation for preventing or decreasing graft rejection in a human recipient of a transplant, wherein the recipient is conditioned under lethal or sublethal conditions, wherein the transplant is derived from a donor which is allogeneic with respect to the recipient, wherein the cell preparation comprises non-alloreactive anti-third party cytotoxic T-lymphocytes (CTLs), wherein the cell preparation does not comprises T-lymphocytes capable of developing into anti-recipient CTLs, and wherein the cell preparation does not substantially comprise CD4+ cells and/or CD56+ cells, the method comprising:

(i) directing peripheral blood lymphocytes derived from the donor against a third party antigen or antigens, wherein said third party antigen or antigens are allogeneic cells, thereby generating third party antigen-treated lymphocytes which comprise anti-third party CTLs;

(ii) substantially depleting said peripheral blood lymphocytes derived from the donor of CD4+ cells and/or CD56+ cells; and (iii) substantially depleting, by deprivation of exogenous IL-2, said third party antigen-treated lymphocytes of T-lymphocytes capable of developing into anti-recipient CTLs, thereby producing the cell preparation.

53. The method of claim 52, wherein step (ii) is effected by substantially depleting said peripheral blood lymphocytes derived from the donor of CD56+ cells or CD4+ cells.

54. The method of claim 52, wherein said third party allogenic cells have HLA antigens which are different from HLA antigens of the donor and which are not cross reactive with HLA antigens of the recipient.

55. The method of claim 52, wherein said third party cells are stimulatory allogenic cells selected from the group consisting of cells purified from peripheral blood lymphocytes, cells purified from spleen, cells purified from lymph nodes, cytokine-mobilized PBLs and in vitro expanded antigen-presenting cells (APC).

* * * * *

UNITED STATES PATENT AND TRADEMARK OFFICE
CERTIFICATE OF CORRECTION

PATENT NO. : 7,270,810 B2  Page 1 of 1
APPLICATION NO. : 10/169028
DATED : September 18, 2007
INVENTOR(S) : Yair Reisner et al.

It is certified that error appears in the above-identified patent and that said Letters Patent is hereby corrected as shown below:

Correct column 1, line 10, as follows:

--and is a continuation-- and delete "~~which claims the benefit~~"

In column 1, lines 12 and 13, delete:

"~~The contents of the above Applications are hereby incorporated by reference~~"

Signed and Sealed this

Twenty-fourth Day of March, 2009

JOHN DOLL
*Acting Director of the United States Patent and Trademark Office*